(12) United States Patent
Chai et al.

(10) Patent No.: US 11,815,448 B2
(45) Date of Patent: Nov. 14, 2023

(54) METHOD, REAGENT, AND CHIP FOR MEASURING ANALYTE CONCENTRATION IN SPECIMEN

(71) Applicant: TERUMO KABUSHIKI KAISHA, Tokyo (JP)

(72) Inventors: Fumihiko Chai, Nakakoma-gun (JP); Takeyuki Moriuchi, Nakakoma-gun (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 572 days.

(21) Appl. No.: 16/988,345

(22) Filed: Aug. 7, 2020

(65) Prior Publication Data

US 2020/0371020 A1    Nov. 26, 2020

Related U.S. Application Data

(63) Continuation of application No. PCT/JP2018/048259, filed on Dec. 27, 2018.

(30) Foreign Application Priority Data

Mar. 7, 2018  (JP) ................. 2018-040887

(51) Int. Cl.
*C07D 519/00* (2006.01)
*C12Q 1/54* (2006.01)
(Continued)

(52) U.S. Cl.
CPC ........... *G01N 21/31* (2013.01); *C07D 519/00* (2013.01); *C12N 9/0004* (2013.01);
(Continued)

(58) Field of Classification Search
CPC ........ G01N 21/31; G01N 21/78; G01N 33/66; G01N 33/52; C07D 519/00; C07D 417/04;
(Continued)

(56) References Cited

U.S. PATENT DOCUMENTS

| 4,290,772 A | 9/1981 | Frey |
| 2007/0105230 A1 | 5/2007 | Perez et al. |

(Continued)

FOREIGN PATENT DOCUMENTS

| JP | 2007-020581 A | 2/2007 |
| JP | 2008-148656 A | 7/2008 |

(Continued)

OTHER PUBLICATIONS

WO2017134878A1—machine translation (Year: 2016).*

(Continued)

*Primary Examiner* — Jennifer Wecker
*Assistant Examiner* — Ali Husain Faraz
(74) *Attorney, Agent, or Firm* — Foley & Lardner LLP

(57) ABSTRACT

Provided is a means capable of measuring an analyte concentration with high accuracy without requiring fractionation of a biological component. The present invention relates to a method for measuring an analyte concentration in a specimen, including (1) preparing the specimen, (2) mixing a coloring reagent, an oxidoreductase, and a light-scattering adjustment reagent with the specimen to obtain an analysis sample having substantially the same scattered light as the specimen, and (3) measuring the analyte concentration by using the analysis sample.

15 Claims, 10 Drawing Sheets

(51) Int. Cl.

| | | |
|---|---|---|
| *G01N 21/78* | (2006.01) | |
| *G01N 21/31* | (2006.01) | |
| *C12N 9/02* | (2006.01) | |
| *C12N 11/096* | (2020.01) | |

(52) U.S. Cl.
CPC .............. *C12N 11/096* (2020.01); *C12Q 1/54* (2013.01); *G01N 21/78* (2013.01)

(58) Field of Classification Search
CPC ...... C12N 9/0004; C12N 11/096; C12Q 1/54; C12Q 1/32; C12Q 1/26; C12M 1/34
See application file for complete search history.

(56) References Cited

U.S. PATENT DOCUMENTS

| | | |
|---|---|---|
| 2007/0154975 A1 | 7/2007 | Watzele et al. |
| 2009/0026094 A1 | 1/2009 | Deng et al. |
| 2012/0022116 A1 | 1/2012 | Deng et al. |

FOREIGN PATENT DOCUMENTS

| | | |
|---|---|---|
| JP | 2009-515194 A | 4/2009 |
| JP | 2015-179038 A | 10/2015 |
| WO | WO-94/01578 A1 | 1/1994 |
| WO | WO-2006/023927 A1 | 3/2006 |
| WO | WO-2013/095137 A2 | 6/2013 |
| WO | WO-2017/134878 A1 | 8/2017 |
| WO | WO-2018/061484 A1 | 4/2018 |
| WO | WO-2019/012865 A1 | 1/2019 |

OTHER PUBLICATIONS

Extended European Search Report dated Feb. 19, 2021 in corresponding European Patent Application No. 18908586.3.
International Searching Authority, "Written Opinion," issued in connection with International Patent Application No. PCT/JP2018/048259, dated Apr. 9, 2019.
International Searching Authority, "International Search Report," issued in connection with International Patent Application No. PCT/JP2018/048259, dated Apr. 9, 2019.
Chinese Office Action issued in connection with CN Appl. Ser. No. 201880090496.2 dated Nov. 22, 2022.

\* cited by examiner

[FIG. 1]
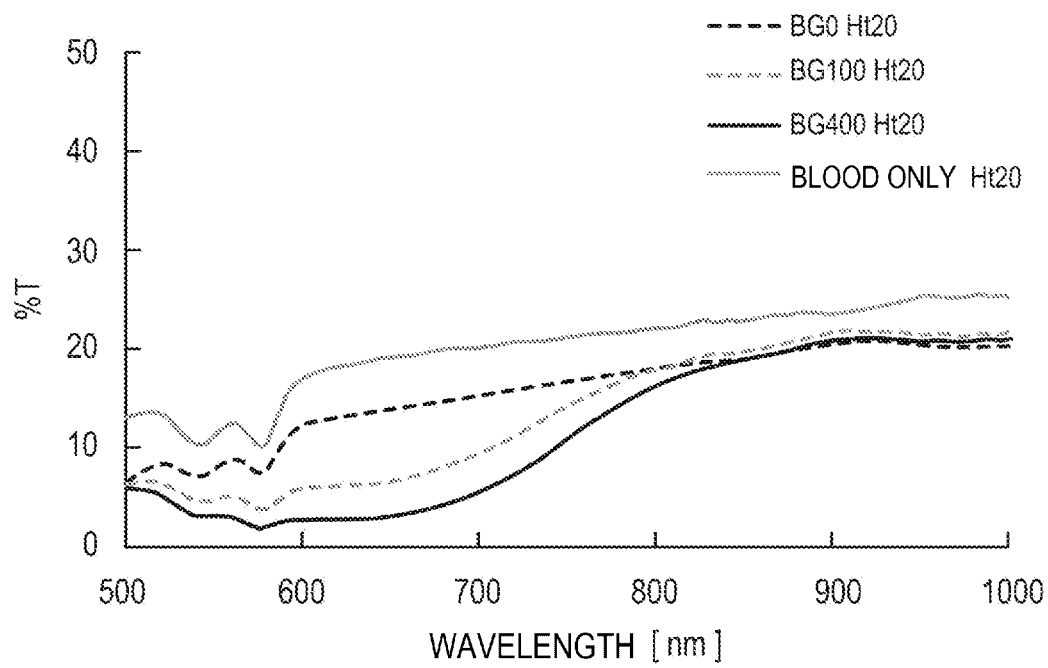
[FIG. 2]
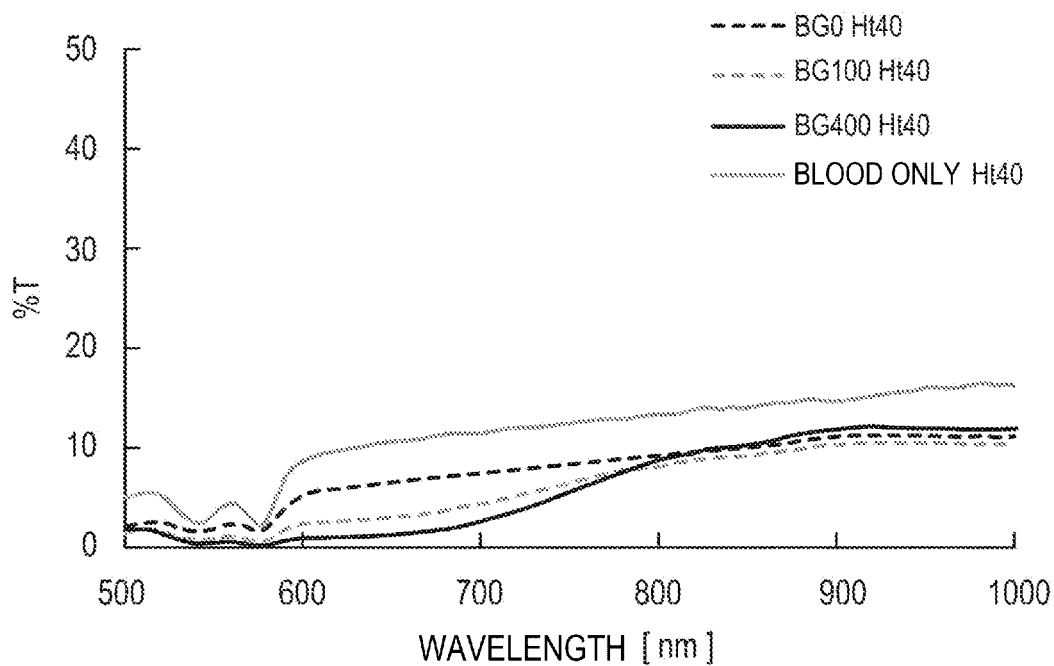

[FIG. 3]
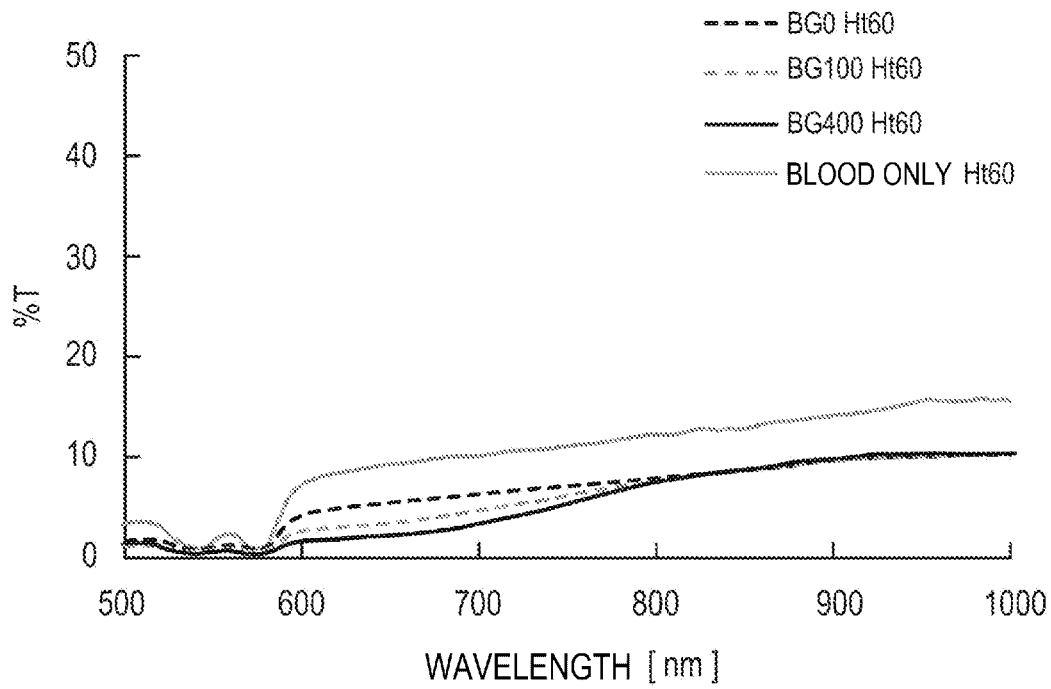
[FIG. 4]
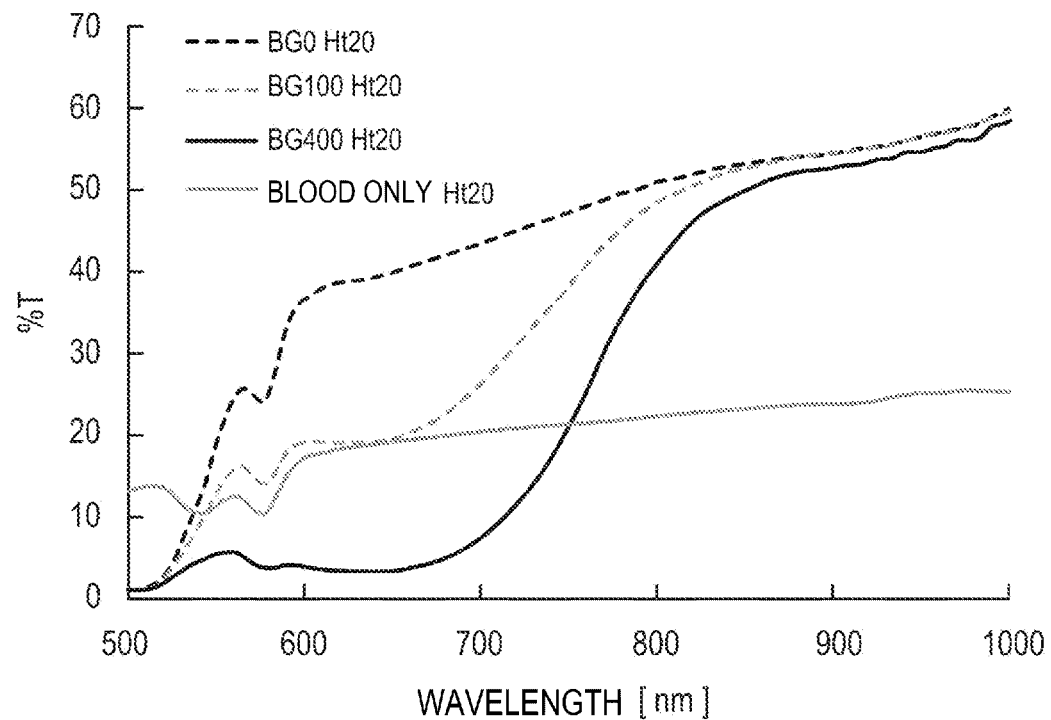

[FIG. 5]
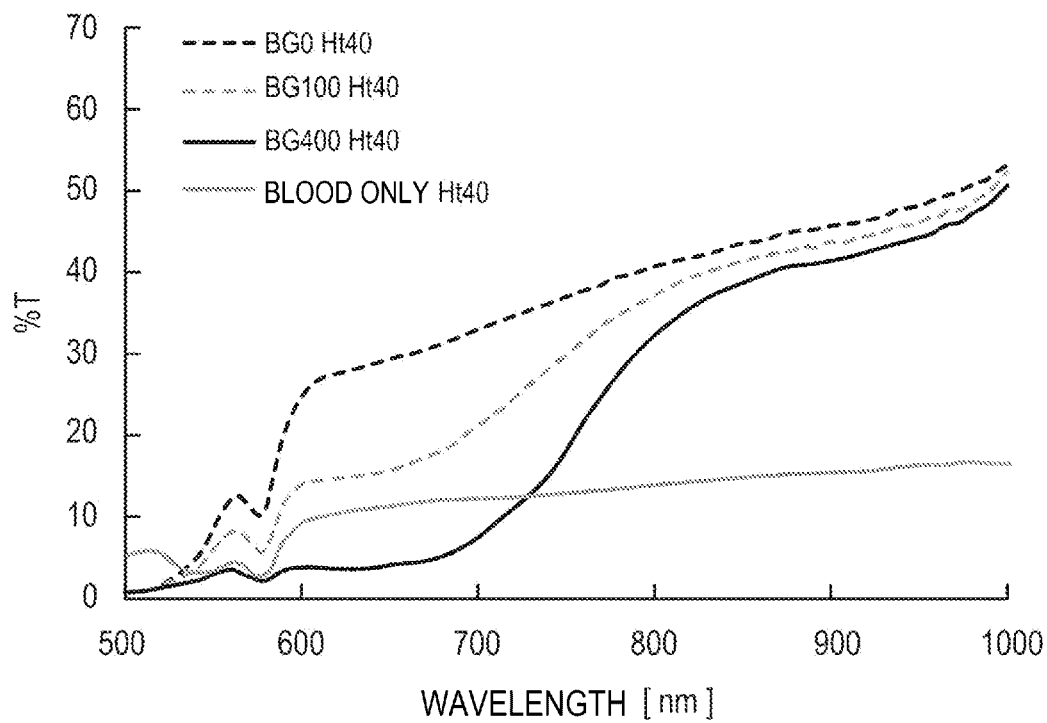
[FIG. 6]
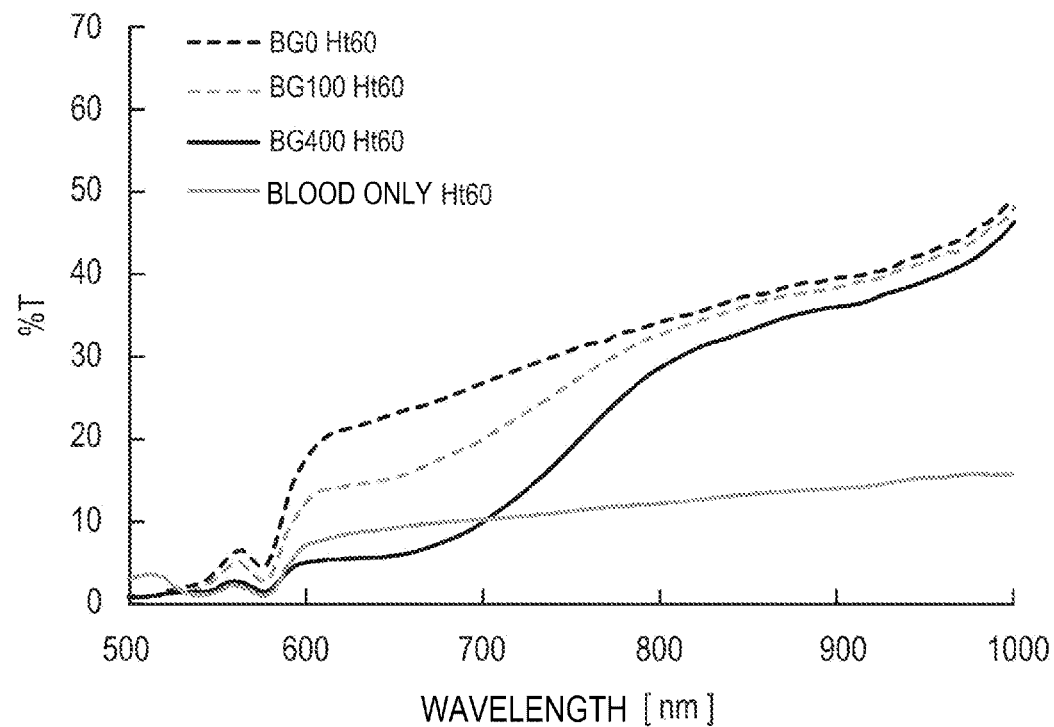

[FIG. 7]
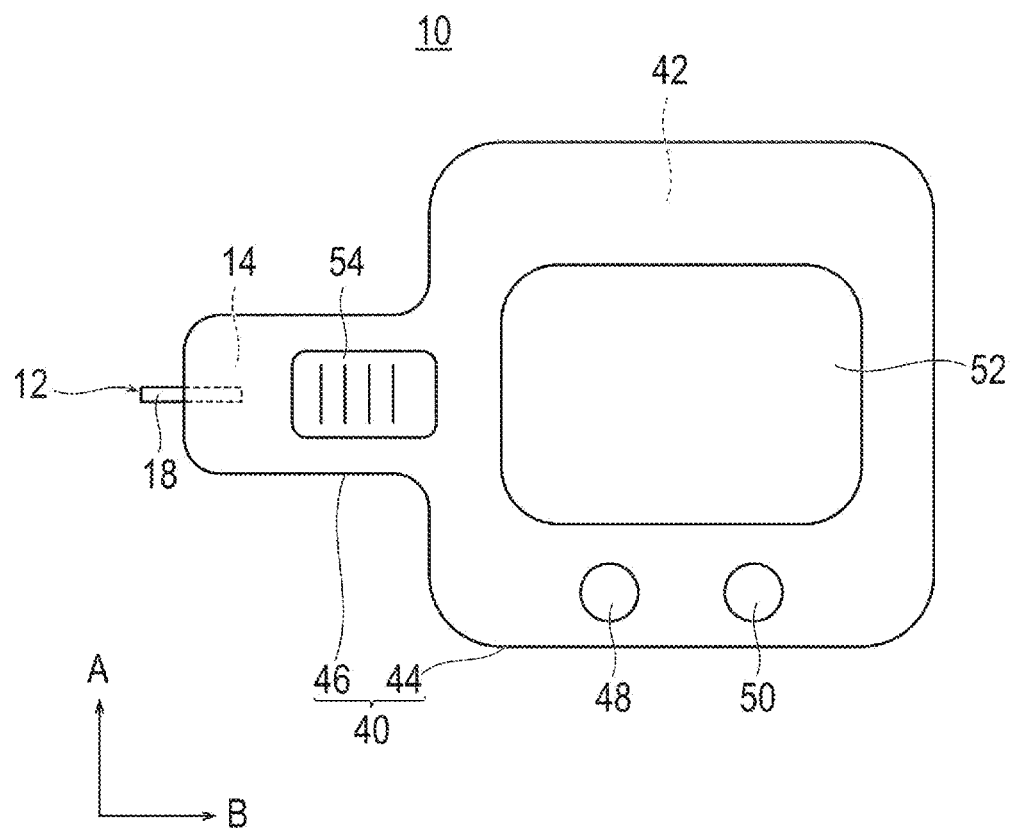

[FIG. 8]
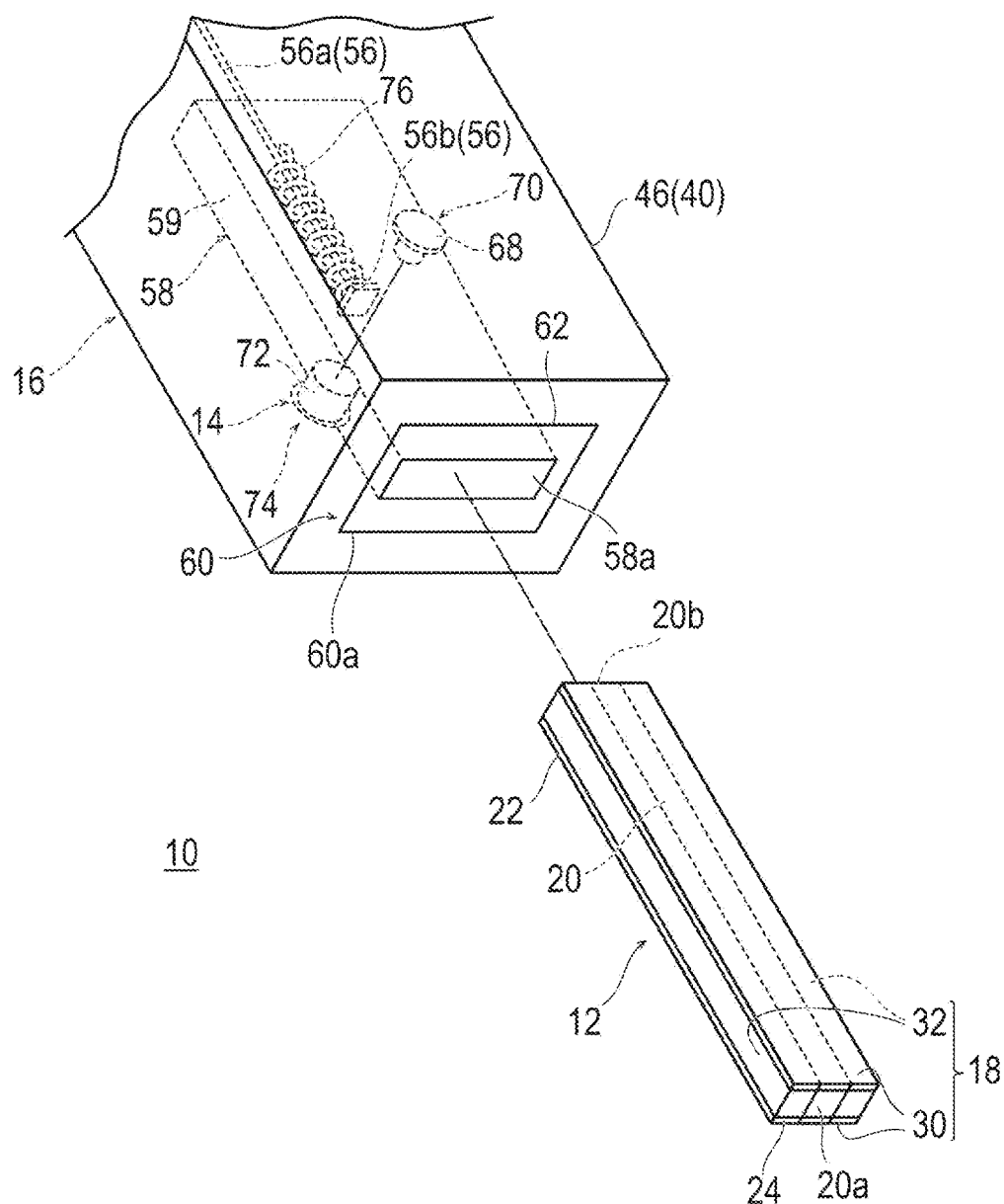

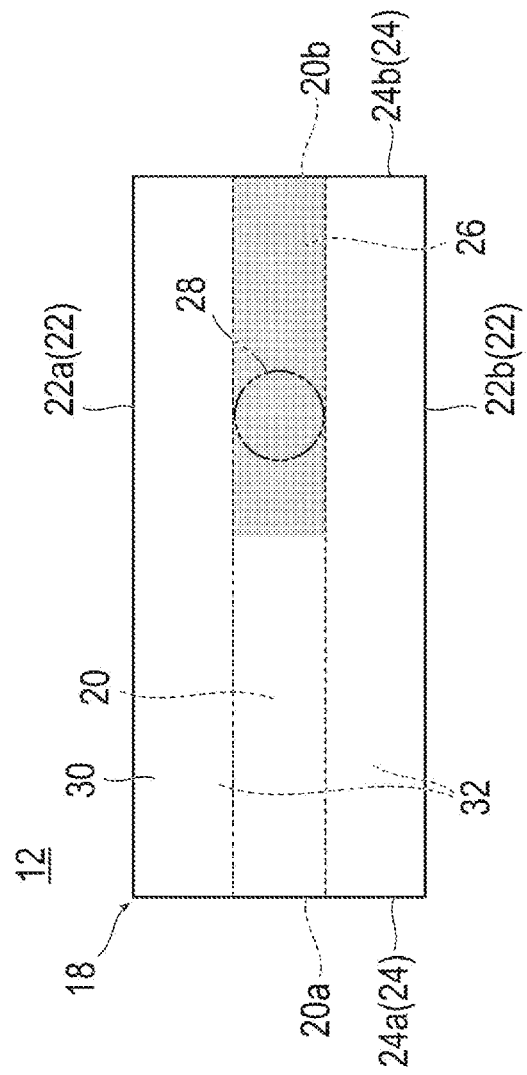
[FIG. 9]

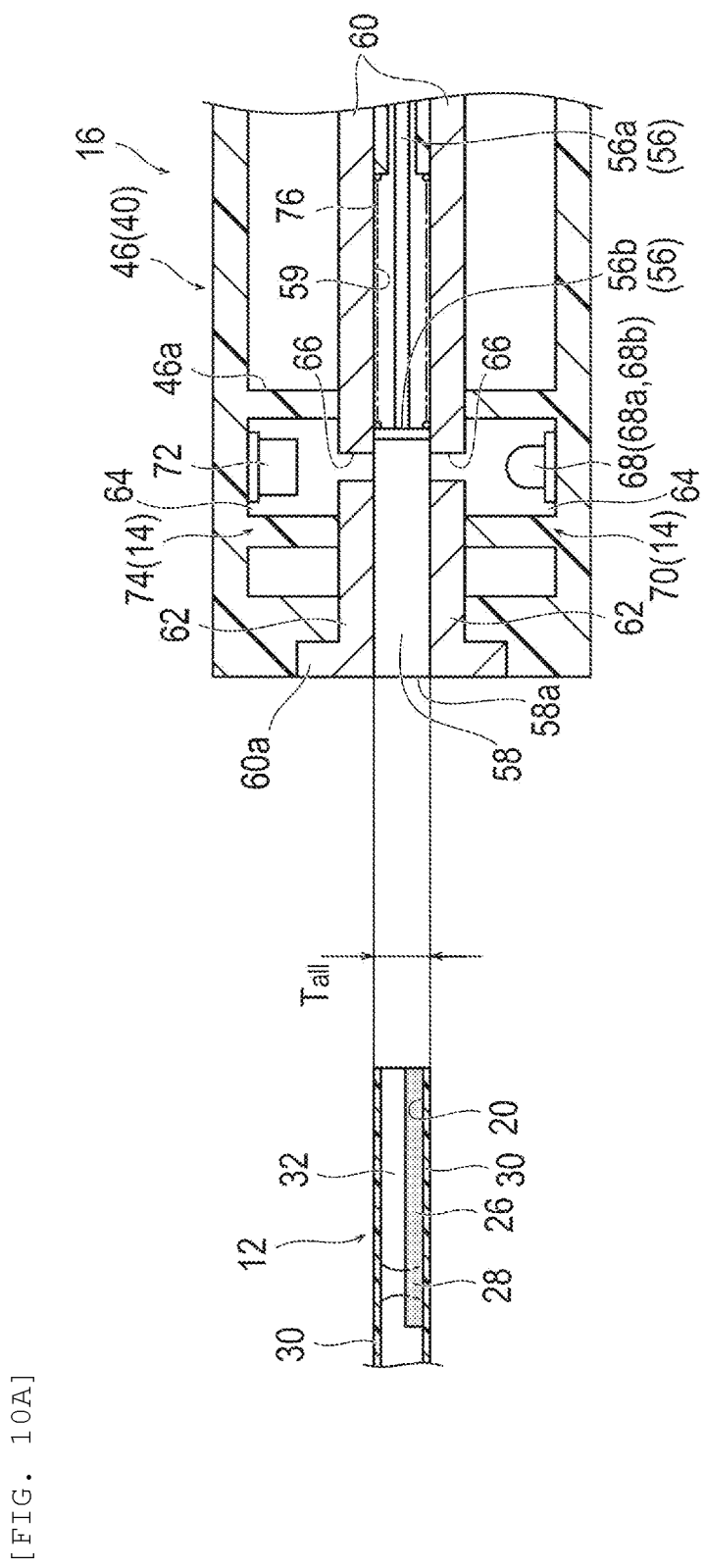
[FIG. 10A]

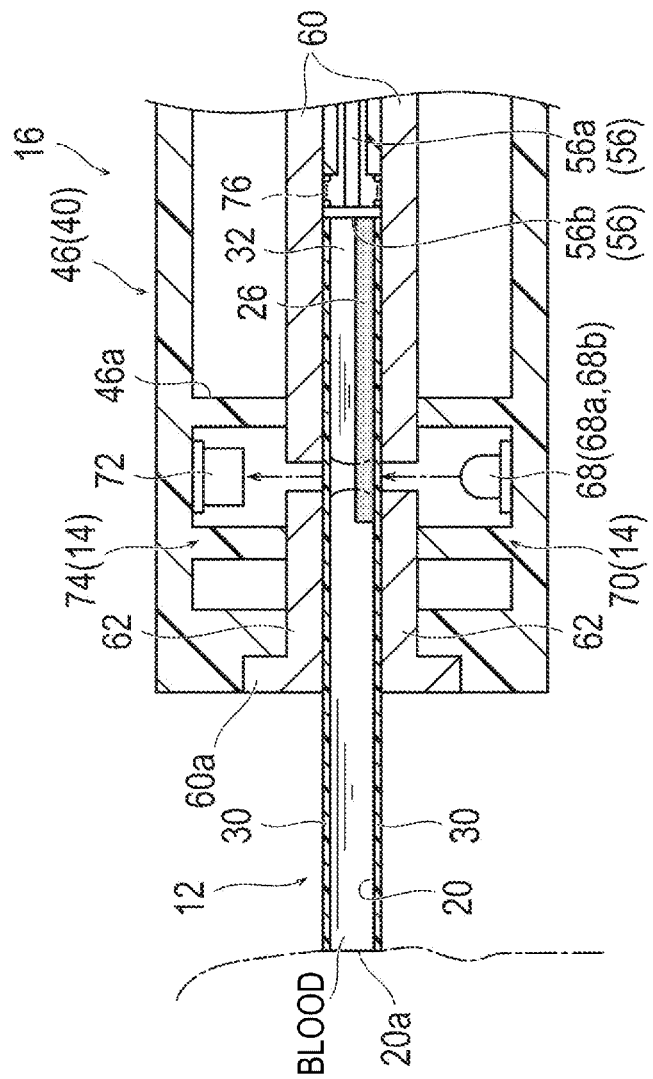

[FIG. 11A]
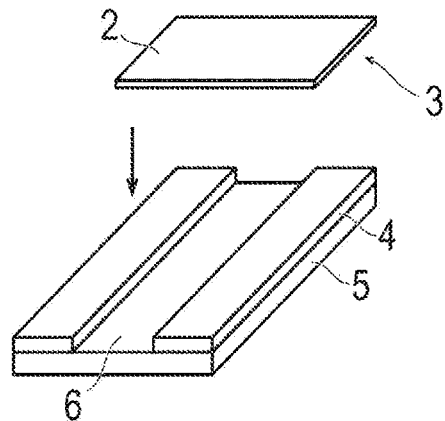
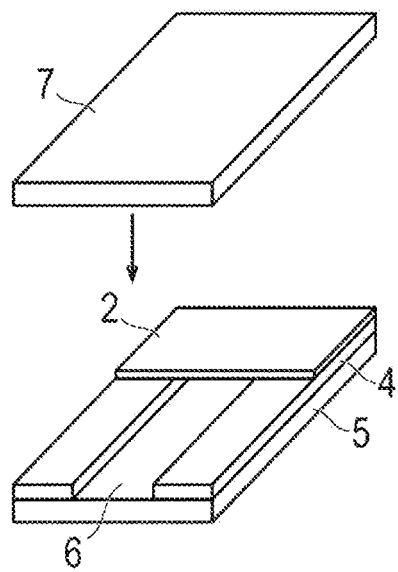

[FIG. 11B]
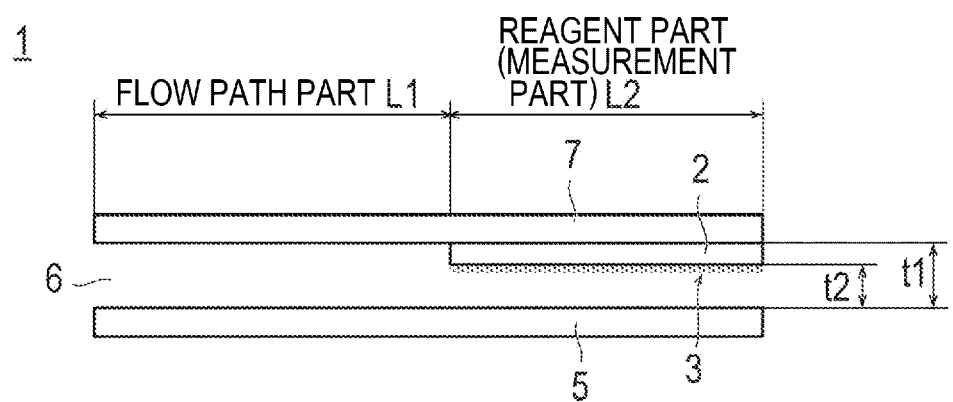
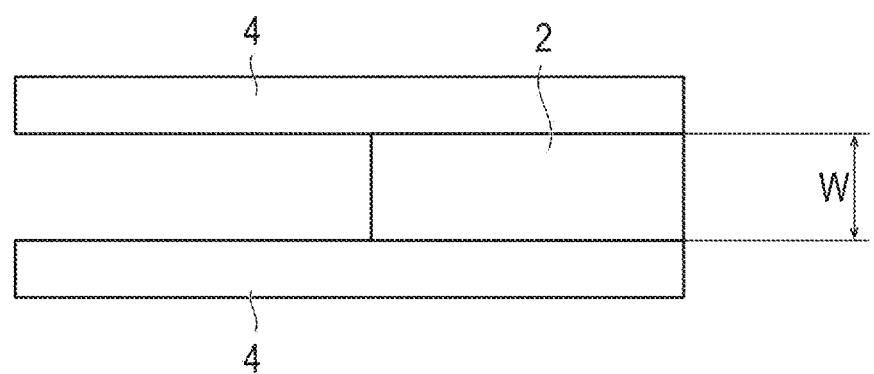

METHOD, REAGENT, AND CHIP FOR MEASURING ANALYTE CONCENTRATION IN SPECIMEN

CROSS-REFERENCE TO RELATED APPLICATIONS

This is a bypass continuation of PCT Application No. PCT/JP2018/048259, filed on Dec. 27, 2018, which claims priority to Japanese Application No. 2018-040887, filed on Mar. 7, 2018. The contents of these applications are hereby incorporated by reference in their entireties.

BACKGROUND

The present invention relates to a method, a reagent, and a chip used for measuring the concentration of an analyte such as glucose contained in a specimen (e.g., a blood sample).

Conventionally, in a clinical chemical test, a technique for measuring an analyte (for example, glucose) contained in a specimen such as blood or urine by an electrochemical method or an optical method (colorimetric method) is known.

For example, JP-A-2008-148656 discloses an invention relating to a dry analytical element for measuring glucose or the like in blood, which is composed of an anisotropic film in which the size of pores on the surface to which a sample is applied is larger than the size of pores on the surface on which color development is detected.

SUMMARY

In the invention described in JP-A-2008-148656, an anisotropic film having a hole with a large diameter on the surface to which a sample is applied and a hole with a small diameter on the surface on which color development is detected is used. As a result, among components derived from blood, components having a large size such as erythrocyte cannot reach the side of the anisotropic membrane where color development is detected, and are filtered out. Therefore, in the invention described in JP-A-2008-148656, a color developing reaction is carried out in the absence of a component having a large size such as erythrocyte. However, when such an anisotropic membrane is used, there is a possibility that the pores are clogged with components, impurities, and the like derived from the sample, which may affect measurement accuracy. In addition, such a method that requires fractionation of components derived from a blood sample may not be sufficient from the viewpoint of rapidity of measurement.

On the other hand, it is known that, when an analyte is measured by an optical method without fractionation of a component derived from a blood sample, a baseline becomes high (that is, noise becomes strong), and it is difficult to perform measurement with high accuracy.

Accordingly, certain embodiments of the present disclosure have been developed in view of the above circumstances, and an object of certain embodiments is to provide a method capable of measuring an analyte concentration with high accuracy without requiring fractionation of a component (biological component) derived from a specimen such as blood.

In order to solve the above-mentioned problems, the present inventors have conducted intensive studies. As a result, the present inventors have found that the above problems can be solved by measuring the concentration of an analyte using an analysis sample in which scattered light before and after mixing of a specimen and a coloring reagent is made substantially the same using a light-scattering adjustment reagent, and have completed the present invention.

A first aspect of the present invention relates to a method for measuring an analyte concentration in a specimen, including:
(1) providing the specimen;
(2) mixing the specimen with a coloring reagent, an oxidoreductase, and a light-scattering adjustment reagent to obtain an analysis sample having substantially the same scattered light as the specimen; and
(3) measuring the analyte concentration by using the analysis sample.

A second aspect of the present invention relates to an analyte concentration measuring reagent, including a coloring reagent, an oxidoreductase, and a light-scattering adjustment reagent.

A third aspect of the present invention relates to a chip for measuring an analyte concentration in a specimen, the chip having a reaction unit, wherein the reaction unit includes a coloring reagent, an oxidoreductase, and a light-scattering adjustment reagent.

BRIEF DESCRIPTION OF THE DRAWINGS

FIG. 1 is a graph showing the transmittance (% T) in the wavelength region of 500 to 1000 nm of the reagents of Example 1 for blood samples having a hematocrit value of 20 and blood glucose concentrations of 0 mg/dl (BG0), 100 mg/dl (BG100), and 400 mg/dl (BG400).

FIG. 2 is a graph showing the transmittance (% T) in the wavelength region of 500 to 1000 nm of the reagents of Example 1 for blood samples having a hematocrit value of 40 and blood glucose concentrations of 0 mg/dl (BG0), 100 mg/dl (BG100), and 400 mg/dl (BG400).

FIG. 3 is a graph showing the transmittance (% T) in the wavelength region of 500 to 1000 nm of the reagents of Example 1 for blood samples having a hematocrit value of 60 and blood glucose concentrations of 0 mg/dl (BG0), 100 mg/dl (BG100), and 400 mg/dl (BG400).

FIG. 4 is a graph showing the transmittance (% T) in the wavelength region of 500 to 1000 nm of the reagents of Comparative Example 1 for blood samples having a hematocrit value of 20 and blood glucose concentrations of 0 mg/dl (BG0), 100 mg/dl (BG100), and 400 mg/dl (BG400).

FIG. 5 is a graph showing the transmittance (% T) in the wavelength region of 500 to 1000 nm of the reagents of Comparative Example 1 for blood samples having a hematocrit value of 40 and blood glucose concentrations of 0 mg/dl (BG0), 100 mg/dl (BG100), and 400 mg/dl (BG400).

FIG. 6 is a graph showing the transmittance (% T) in the wavelength region of 500 to 1000 nm of the reagents of Comparative Example 1 for blood samples having a hematocrit value of 60 and blood glucose concentrations of 0 mg/dl (BG0), 100 mg/dl (BG100), and 400 mg/dl (BG400).

FIG. 7 is a plan view schematically showing a blood glucose meter (component measuring device) to which a measuring chip according to the present embodiment is attached.

FIG. 8 is an enlarged perspective view showing the measuring chip and the optical measurement unit of the device main body shown in FIG. 7.

FIG. 9 is a side view showing the measuring chip of FIG. 7.

FIG. 10A is a first plan view showing the attachment operation of the measuring chip and the device main body of FIG. 7.

FIG. 10B is a second plan sectional view showing the attachment operation subsequent to FIG. 10A.

FIG. 11A is a pattern diagram of a blood glucose meter sensor used in Examples and Comparative Examples.

FIG. 11B is a diagram for explaining the length, width, and thickness of the inner surface of the blood glucose meter sensor of FIG. 11A.

DETAILED DESCRIPTION

A first aspect of the present invention relates to a method for measuring an analyte concentration in a specimen, including:
 (1) providing the specimen;
 (2) mixing the specimen with a coloring reagent, an oxidoreductase, and a light-scattering adjustment reagent to obtain an analysis sample having substantially the same scattered light as the specimen; and
 (3) measuring the analyte concentration by using the analysis sample.

A second aspect of the present invention relates to an analyte concentration measuring reagent, including a coloring reagent, an oxidoreductase, and a light-scattering adjustment reagent.

A third aspect of the present invention relates to a chip for measuring an analyte concentration in a specimen, the chip having a reaction unit, wherein the reaction unit includes a coloring reagent, an oxidoreductase, and a light-scattering adjustment reagent.

In the present specification, the above description of a certain aspect of the present invention can be applied to other aspects with appropriate modifications.

According to certain embodiments of the present invention, the analyte concentration can be measured with high accuracy without requiring fractionation of components (biological components) derived from a specimen such as blood. The present inventors have made various studies on the cause of deterioration of measurement accuracy due to an increase in baseline when an analyte is measured by an optical method without fractionation of a biological component derived from a specimen (for example, a blood sample). For example, when the specimen is a blood sample, if the analyte is measured by an optical method without fractionation of components derived from the blood sample, scattered light is generated due to the refractive index difference between the erythrocyte and the extracellular fluid of erythrocyte (i.e., components other than erythrocyte present in the sample). As a result, the present inventors have found that the base line derived from the scattered light becomes high and the measurement accuracy is lowered. In order to solve such a problem, the present inventors have found that it is effective to use a light-scattering adjustment reagent so that the scattered light is substantially the same between the specimen and the analysis sample. Hereinafter, a case where the specimen is a blood sample will be described in detail.

Usually, due to the presence of hemoglobin or the like, the refractive index in erythrocyte is higher than the refractive index of extracellular fluid of erythrocyte. When a reagent such as a coloring reagent is added to blood (whole blood), the osmotic pressure of the extracellular fluid of erythrocyte increases with the dissolution of the reagent. On the other hand, as the osmotic pressure of the extracellular fluid of erythrocyte increases, the erythrocytes shrink due to the difference in osmotic pressure between the erythrocyte and the extracellular fluid of erythrocyte, and thus the refractive index of the intracellular fluid of erythrocyte further increases. Here, by further adding a substance having a high refractive index to the reagent, it is possible to intentionally promote an increase in the refractive index of the extracellular fluid of erythrocyte to make the refractive index inside and outside the erythrocytes substantially the same, thereby adjusting the refractive index difference inside and outside the erythrocytes. However, when the specimen is a blood sample, the degree of decrease in the refractive index of the extracellular fluid of erythrocyte varies depending on the hematocrit value or the dilution effect of the extracellular fluid of erythrocyte due to the release of the intracellular fluid of erythrocyte (water). For this reason, it has been difficult to adjust the refractive indices of the inside and outside of the erythrocytes to be the same for blood samples having a wide range of hematocrit values. As a result of intensive studies to solve the above problems, it has been found that it is effective to minimize a change in the refractive index difference before and after mixing the reagent. As a result of further intensive studies on the above means, it has been found that it is effective in measurement of a blood sample to suppress the change in the refractive index ($n_{RBC-1}$) in erythrocytes before the addition of the reagent and the refractive index ($n_{RBC-2}$) in erythrocytes after the addition of the reagent (i.e., $\Delta n_{RBC} = n_{RBC-1} - n_{RBC-2}$) and the change in the refractive index ($n_{S-1}$) of the extracellular fluid of erythrocyte before the addition of the reagent and the refractive index ($n_{S-2}$) of the extracellular fluid of erythrocyte after the addition of the reagent (i.e., $\Delta n_S = n_{S-1} - n_{S-2}$), respectively, to a low level by using the light-scattering adjustment reagent. Further, in the present invention, by using the light-scattering adjustment reagent, the shrinkage of the erythrocytes is adjusted so that the refractive index change amount ($\Delta n_{RBC} = n_{RBC-1} - n_{RBC-2}$) in the erythrocytes and the refractive index change amount ($\Delta n_S = n_{S-1} - n_{S-2}$) of the extracellular fluid of erythrocyte before and after mixing the reagent become substantially the same, whereby the two refractive index change amounts before and after mixing the reagent can be made substantially the same. As described above, by reducing the variation in the refractive index difference between the erythrocyte and the extracellular fluid of erythrocyte before and after mixing the reagent, as a result, the scattered light before and after mixing the reagent can be made substantially the same (the scattering change of the light can be suppressed), so that the measurement error can be reduced. In addition, the measurement accuracy of the analyte can be improved even in blood samples having a wide range of hematocrit values. The above effects can be achieved particularly effectively when the light-scattering adjustment reagent is used in combination with a transition metal compound. It should be noted that the above-described mechanism is a presumption and does not limit the technical scope of the present invention.

In the present specification, the "extracellular fluid of erythrocyte" means a fraction other than erythrocytes, and means a component (plasma) derived from a blood sample other than erythrocytes before mixing the reagent, and means a liquid containing a component (plasma) derived from a blood sample other than erythrocytes, a coloring reagent, an oxidoreductase, a light-scattering adjustment reagent, and other substances (for example, a transition metal compound) that can be optionally used after mixing the reagent. In addition, in the present specification, a mixture containing a coloring reagent, an oxidoreductase, a light-scattering adjustment reagent, and other substances (for example, a transition metal compound) that may be optionally used is also referred to as an "analyte concentration measuring reagent" or simply as a "reagent".

Hereinafter, embodiments of the present invention will be described. The present invention is not limited to the following embodiments. In addition, dimensional ratios in the drawings are exaggerated for convenience of description and may be different from actual ratios.

In the present specification, "X to Y" indicating a range includes X and Y, and means "X or more and Y or less". Unless otherwise specified, operations and measurements of physical properties and the like are performed under conditions of room temperature (20 to 25° C.)/relative humidity of 40 to 50% RH.

<Method for Detecting Analyte in Blood Sample>

One aspect of the present invention relates to a method for measuring an analyte concentration in a specimen, including:

(1) providing the specimen (step (1));
(2) mixing the specimen with a coloring reagent, an oxidoreductase, and a light-scattering adjustment reagent to obtain an analysis sample having substantially the same scattered light as the specimen (step (2)); and
(3) measuring the analyte concentration by using the analysis sample (step (3)). According to the method of one aspect of the present invention, even in a specimen (for example, a sample containing erythrocytes) that induces light scattering, an analyte can be detected with high accuracy without requiring fractionation of a biological component.

[Step (1)]

In this step, a specimen is prepared. Here, the specimen (biological component measurement target) is not particularly limited as long as it contains a target analyte (biological component). Specific examples thereof include blood and body fluids such as urine, saliva, and interstitial fluid. Of these, blood, particularly whole blood, is preferred as the specimen. The source of the specimen is not particularly limited. The specimen may be derived from a human or non-human animal. Examples of non-human animals include, but are not limited to, laboratory animals such as mice, rats, and hamsters; pets such as dogs, cats, and rabbits; and livestock and poultry such as pigs, cows, goats, sheep, horses, and chickens. Preferably, the specimen is derived from a human. That is, the specimen is preferably human blood, and particularly preferably human whole blood.

The method for preparing the specimen is not particularly limited. For example, a known method such as separation of plasma from blood can be applied, but a specimen may be used as it is. In a particularly preferred embodiment, the specimen is peripheral blood or venous blood taken from a human.

[Step (2)]

In this step, the specimen prepared in step (1) is mixed with a coloring reagent, an oxidoreductase, and a light-scattering adjustment reagent to obtain an analysis sample having scattered light substantially the same as that of the specimen.

In this step (2), by using the light-scattering adjustment reagent, the scattered light in the specimen and the scattered light in the analysis sample can be made substantially the same. Specifically, for example, in the case where the specimen is a blood sample, when a reagent such as a coloring reagent is added to the blood sample, the refractive index difference between the intracellular fluid of erythrocyte and the extracellular fluid of erythrocyte increases. On the other hand, when the light-scattering adjustment reagent is used in combination, the refractive index changes of the intracellular fluid of erythrocyte and the extracellular fluid of erythrocyte before and after mixing the reagent can be suppressed to a low level, and as a result, the shrinkage of the erythrocytes can be appropriately adjusted so that the refractive index change ($\Delta n_{RBC}$) in the erythrocytes and the refractive index change ($\Delta n_S$) of the extracellular fluid of erythrocyte before and after mixing the reagent are substantially the same. Therefore, the refractive index difference between the erythrocyte and the extracellular fluid of erythrocyte before and after mixing the reagent is reduced, and as a result, the scattered light before and after mixing the reagent can be made substantially the same (the scattering change of the light can be suppressed). Therefore, in the next step (3), the analyte concentration in the specimen can be measured with high accuracy. It should be noted that the above-described mechanism is a presumption and does not limit the technical scope of the present invention.

The "light-scattering adjustment reagent" in the present specification is not particularly limited as long as it can make the scattered light of the analysis sample substantially the same as that of the specimen. Here, "the scattered light of the analysis sample is substantially the same as that of the specimen" means that the average transmittance before and after mixing the reagent is substantially the same in a wavelength region substantially free from the influence of components constituting the reagent (a coloring reagent, an oxidoreductase, a light-scattering adjustment reagent, and other substances such as a transition metal compound that can be optionally used), particularly the coloring reagent. Here, the "wavelength region substantially free from the influence of the coloring reagent" refers to a wavelength region on the longer wavelength side among wavelength regions in which the absorbance of the dye component generated by the reaction with the substance to be measured is 3% or less, preferably 1% or less of the absorbance at the measurement wavelength. In the present invention, such a wavelength region is preferably 800 to 1000 nm, and in particular, the wavelength region of 850 to 1000 nm is not affected by the coloring reagent that has reacted with the substance to be measured (see FIGS. 1 to 6). Therefore, in the present specification, the wavelength region in which the influence of the coloring reagent does not substantially exist is set to "850 to 1000 nm". In view of the above, in the present specification, "the scattered light of the analysis sample is substantially the same as that of the specimen" means that the difference ($=\text{aveT}_{analyte}(\%)-\text{aveT}_{Sample}(\%)$) between the average transmittance ($\text{aveT}_{analyte}(\%)$) of the analysis sample after mixing the reagent in the wavelength region 850 to 1000 nm and the average transmittance ($\text{aveT}_{Sample}(\%)$) of the specimen before mixing the reagent in the wavelength region 850 to 1000 nm is more than −15.0% and less than 15.0%. In the present specification, the difference ($=\text{aveT}_{analyte}(\%)-\text{aveT}_{Sample}(\%)$) between the average transmittance ($\text{aveT}_{analyte}(\%)$) of the analysis sample after mixing the reagent in the wavelength region 850 to 1000 nm and the average transmittance ($\text{aveT}_{Sample}(\%)$) of the specimen before mixing the reagent in the wavelength region 850 to 1000 nm is also simply referred to as "average transmittance difference". The average transmittance difference is preferably −10% to 10%, more preferably −9.0% to 9.0%, and particularly preferably more than −7.5% and less than 7.5%. That is, in a preferred embodiment of the present invention, in the step (2), the difference ($=\text{aveT}_{analyte}(\%)-\text{aveT}_{Sample}(\%)$) between the average transmittance ($T_{analyte}$(%)) of the analysis sample in the wavelength region 850 to 1000 nm and the average transmittance ($T_{Sample}$(%)) of the specimen in the wavelength region 850 to 1000 nm is −10% or more and 10% or less. In a more preferred embodiment of the present invention, in the step (2), the difference (=ave$T_{analyte}$(%)−ave$T_{Sample}$(%)) between the average transmittance ($T_{analyte}$(%)) of the analysis sample in the wavelength region 850 to 1000 nm and the average transmittance ($T_{Sample}$(%)) of the specimen in the wavelength region 850 to 1000 nm is −9.0% or more and 9.0% or less.

In the present specification, with respect to a sample (specimen, analysis sample), a transmittance spectrum was continuously measured in a wavelength region of 850 nm to 1000 nm, and in the obtained spectrum, a transmittance at least for each 1 nm (that is, measurement width ≤1 nm) was measured. The "average transmittance" is determined by calculating the difference in transmittance at each wavelength according to the following formula (A) and calculating the average of these transmittance differences.

[Math. 1]

$$\text{Transmittance difference (\%)} = T_{analyte}(\%) - T_{Sample}(\%) \quad \text{Formula (A)}$$

In the above formula (A),
$T_{analyte}$ represents the transmittance (%) of the analysis sample at a predetermined wavelength, and
$T_{Sample}$ represents the transmittance (%) of the specimen at a predetermined wavelength.

In the present specification, the "transmittance" and "absorbance" of a specimen or an analysis sample are values measured at a light path length of 50 μm or values corrected to a light path length of 50 μm. For example, it can be determined by the following spectral analysis using a blood glucose level detection chip (spacer thickness: 50 μm).

<Spectrum Analysis>

The outline of the evaluation system used for the spectrum measurement is shown below. The outline of the evaluation system is shown below:

[Chem. 1]

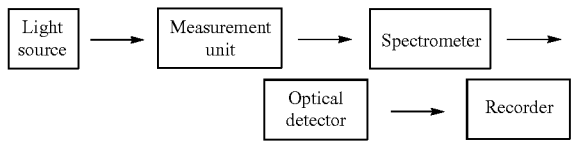

(Outline of Evaluation System)
Light source: Halogen light source SPL-2H (KLV Co., Ltd.)
Fiber connector: SMA
Compatible fiber: Core diameter=200μ or more
Spectrometer: Small fiber optical spectroscope USB2000+ (Ocean Optics)
Detector range: 200 to 1100 nm For example, a blood glucose level detection chip (spacer thickness (flow path thickness): 50 μm, reagent layer thickness: 1 μm to 4 μm) as described in Examples is produced using the analyte concentration measuring reagent. The absorbance (measured value) is measured using this blood glucose level detection chip. At this time, the measured value is a measured value of absorbance obtained by using a difference (clearance) between the flow path thickness and the reagent layer thickness as a light path length. The absorbances (measured values) at the measurement wavelengths (400 to 1000 nm) are corrected when the light path length is 50 μm, and the transmittance (T (%)) is determined from the corrected absorbances (Abs) according to the following formula (B). The absorbance is corrected by dividing the absorbance (measured value) at each measurement wavelength by the value of the clearance (CL) (μm) measured at each chip and multiplying the result by 50 (μm).

[Math. 2]

$$\text{Transmittance } T(\%) = \frac{100}{10^{Abs}} \quad \text{Formula (B)}$$

In the above formula (B), Abs represents the absorbance after correction.

Next, a blood sample is applied to the above-described blood glucose level detection chip, and a spectrum analysis is performed 5 to 15 seconds (for example, 9 seconds) after the applying. On the basis of the obtained spectrum analysis result, the absorbance is corrected in the same manner as before the applying to obtain the transmittance.

Note that the method according to one aspect of the present invention is not limited to the method using a detection chip described in the Examples. For example, in the case of analysis using a cell having a light path length of 10 mm, the "transmittance (%)" may be determined from the absorbance determined by performing correction in consideration of the concentration of the analyte in the blood sample present in the measurement cell according to the Lambert-Beer law.

In addition, as described above, in the present invention, the average transmittance difference is more than −15.0% and less than 15.0%, but preferably, the transmittance before and after mixing the reagent is substantially the same in the entire wavelength region in which there is substantially no influence by the components constituting the reagent, particularly the coloring reagent. That is, the absolute value of the difference (=$T_{analyte}$(%)−$T_{Sample}$(%)) between the transmittance ($T_{analyte}$(%)) of the analysis sample after mixing the reagent in the entire wavelength region 850 to 1000 nm and the transmittance ($T_{Sample}$(%)) of the specimen before mixing the reagent in the entire wavelength region 850 to 1000 nm is preferably 10% or less, more preferably 9.0% or less, and particularly preferably less than 7.5%. In the present specification, the absolute value of the difference (=$T_{analyte}$(%)−$T_{Sample}$(%)) between the transmittance ($T_{analyte}$(%)) of the analysis sample after mixing the reagent in the entire wavelength region 850 to 1000 nm and the transmittance ($T_{Sample}$(%)) of the specimen before mixing the reagent in the entire wavelength region 850 to 1000 nm is also simply referred to as "transmittance difference (absolute value)" or "transmittance difference".

In the present specification, the transmittance difference (absolute value) is obtained by continuously measuring a transmittance spectrum in the wavelength region of 850 nm to 1000 nm for a sample (specimen, analysis sample), measuring the transmittance at least for each 1 nm (that is, measurement width≤1 nm) in the obtained spectrum, calculating the transmittance difference at each wavelength as an absolute value according to the following formula (C), obtaining the maximum value thereof, and evaluating whether or not the maximum value is within the specific range. That is, in the present specification, "the transmittance difference (absolute value) is 10% or less" means that the maximum value is 10% or less (the transmittance difference is 10% or less at all the measurement points) except for measurement errors and outliers.

[Math. 3]

$$\text{Transmittance difference (\%)} = |T_{analyte}(\%) - T_{Sample}(\%)| \qquad \text{Formula (C)}$$

In the above formula (C),
$T_{analyte}$ represents the transmittance (%) of the analysis sample at a predetermined wavelength, and
$T_{Sample}$ represents the transmittance (%) of the specimen at a predetermined wavelength.

The light-scattering adjustment reagent that can be used in the present invention is not particularly limited as long as the scattered light is substantially the same before and after mixing the analyte concentration measuring reagent as described above. Specific examples thereof include dyes and chromogens represented by the following formula (1), polysaccharides, sugar alcohols, and aromatic hydrocarbon compounds having ionic functional groups such as aromatic hydrocarbons having at least one sulfonic acid group. These compounds may be in the form of a salt, and more specifically, may be a sodium salt, a potassium salt, an ammonium salt, a methylamine salt, an ethylamine salt, a diethylamine salt, a triethylamine salt, a monoethanolamine salt, and halides such as a chloride, but are not limited thereto. Preferably, the salt is a sodium salt or a potassium salt. The above-mentioned light-scattering adjustment reagent may be used alone or in the form of a mixture of two or more kinds. Among these, the light-scattering adjustment reagent is preferably one or more selected from the group consisting of a compound represented by the following formula (1), an aromatic hydrocarbon having at least one sulfonic acid group, a disaccharide, and a salt thereof, and more preferably an aromatic hydrocarbon having at least one sulfonic acid group or a salt thereof. With the preferable light-scattering adjustment reagent, the shrinkage of the erythrocytes can be more appropriately controlled, the scattered light before and after the mixing of the specimen and the analyte concentration measuring reagent can be made the same (the average transmittance difference can be made smaller), and the analyte concentration can be measured with higher accuracy.

As the light-scattering adjustment reagent, a compound represented by the following formula (1) can be used.

[Chem. 2]

$$Q^1-N=N-Q^2 \qquad \text{Formula (1)}$$

In the formula (1), $Q^1$ and $Q^2$ each independently represent an aryl group or a nitrogen-containing heterocyclic group that may have one or more substituents.

In the compound represented by the formula (1), examples of the "aryl group" include a phenyl group, a naphthyl group, an anthracenyl group, and a phenanthryl group, and the aryl group is preferably selected from the group consisting of a phenyl group and a naphthyl group.

In the compound represented by the formula (1), examples of the "nitrogen-containing heterocyclic group" include a pyrrolidyl group, a pyrrolyl group, a piperidyl group, a pyridyl group, an imidazoyl group, a pyrazoyl group, a pyrazolonyl group, an oxazoyl group, a thiazoyl group, a pyrazyl group, an indoyl group, an isoindolyl group, and a benzoimidazoyl group, and the nitrogen-containing heterocyclic group is preferably selected from the group consisting of an imidazoyl group, a pyrazoyl group, and a pyrazolonyl group.

The aryl group and the nitrogen-containing heterocyclic group may have one or more substituents. Here, the substituent is not particularly limited, and for example, the aryl group or the nitrogen-containing heterocyclic group may have one or more substituents selected from the group consisting of a halogen atom (for example, a fluorine atom, a chlorine atom, a bromine atom, or an iodine atom), a hydroxy group, an alkyl group having 1 to 3 carbon atoms (for example, a methyl group, an ethyl group, a n-propyl group, and an isopropyl group), an alkoxy group having 1 to 3 carbon atoms (for example, a methoxy group, an ethoxy group, a n-propoxy group, and an isopropoxy group), a carboxy group, a sulfo group, an amino group, a carbamoyl group, a sulfamoyl group, a phenyl group, a carboxyphenyl group, and a sulfophenyl group. The phenyl group, which is a substituent of the aryl group or the nitrogen-containing heterocyclic group, may be further substituted with one or more substituents selected from the group consisting of a halogen atom (for example, a fluorine atom, a chlorine atom, a bromine atom, an iodine atom), a hydroxy group, an alkyl group having 1 to 3 carbon atoms (for example, a methyl group, an ethyl group, a n-propyl group, and an isopropyl group), an alkoxy group having 1 to 3 carbon atoms (for example, a methoxy group, an ethoxy group, a n-propoxy group, and an isopropoxy group), a carboxy group, a sulfo group, an amino group, a carbamoyl group, a sulfamoyl group, a phenyl group, a carboxyphenyl group, and a sulfophenyl group.

From the viewpoint of highly accurate measurement of the analyte concentration, in a preferred embodiment, $Q^1$ has the following structure:

[Chem. 3]

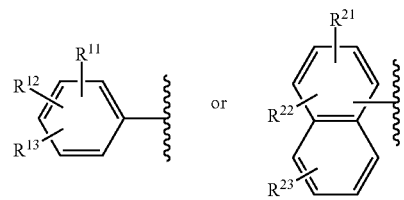

In the above structural formula, $R^{11}$, $R^{12}$, $R^{13}$, $R^{21}$, $R^{22}$, and $R^{23}$ are each independently selected from the group consisting of a hydrogen atom, a halogen atom, a carboxy group, a carboxylate group, a sulfo group, a sulfonate group, a carbamoyl group, and a sulfamoyl group.

From the viewpoint of highly accurate measurement of the analyte concentration, in a preferred embodiment, $Q^2$ has the following structure:

[Chem. 4]

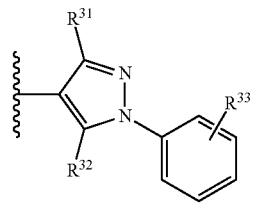

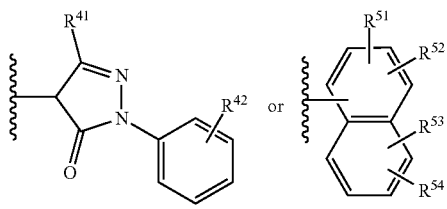

In the above structural formula, $R^{31}$, $R^{32}$, and $R^{41}$ are each independently selected from the group consisting of a hydrogen atom, a hydroxy group, an alkyl group having 1 to 3 carbon atoms, a carboxy group, a carboxylate group, a sulfo group, a sulfonate group, an amino group, a carbamoyl group, and a sulfamoyl group; $R^{33}$ and $R^{42}$ are each independently selected from the group consisting of a hydrogen atom, a carboxy group, a carboxylate group, a sulfo group, and a sulfonate group; and $R^{51}$, $R^{52}$, $R^{53}$, and $R^{54}$ are each independently selected from the group consisting of a hydrogen atom, a halogen atom, a hydroxy group, a carboxy group, a carboxylate group, a sulfo group, a sulfonate group, a carbamoyl group, and a sulfamoyl group.

In a more preferred embodiment, $Q^2$ has the following structure, wherein $R^{31}$, $R^{32}$, and $R^{33}$ are as described above.

[Chem. 5]

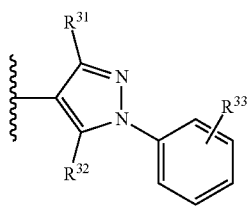

In a preferred embodiment, the compound represented by the formula (1) has the following structure, wherein $R^{11}$, $R^{12}$, $R^{13}$, $R^{31}$, $R^{32}$, $R^{33}$, $R^{41}$, $R^{42}$, $R^{51}$, $R^{52}$, $R^{53}$, and $R^{54}$ are as described above.

[Chem. 6]

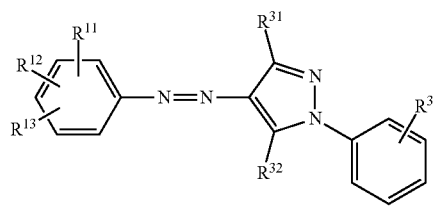

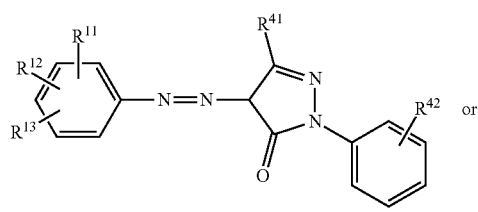

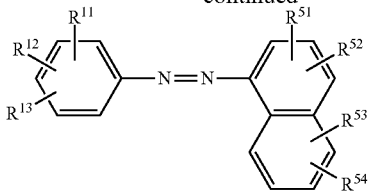

Specific examples of the compound represented by the formula (1) may include Acid Yellow 11, Acid Yellow 23, Acid Yellow 49, Acid Yellow 59, Acid Orange 12, Orange G, Acid Red 18, Acid Red 26, Acid Red 27, Acid Red 88, Solvent Yellow 5, Solvent Yellow 6, Solvent Yellow 11, Food Yellow 3, and Food Yellow 5. Among these, a compound selected from the group consisting of Acid Yellow 11, Acid Yellow 23, Acid Yellow 49, Acid Yellow 59, and Food Yellow 3 is preferably used. In a more preferred embodiment, Acid Yellow 23 is used as the light-scattering adjustment reagent.

The aromatic hydrocarbon having at least one sulfonic acid group used as the light-scattering adjustment reagent is not particularly limited as long as it is an aromatic hydrocarbon having at least one sulfonic acid group, and may be appropriately selected depending on the purpose. Here, the aromatic hydrocarbon is not particularly limited, and examples thereof include benzene, naphthalene, and anthracene, preferably benzene and naphthalene, and more preferably benzene. The number of sulfonic acid groups contained in the aromatic hydrocarbon is not particularly limited and varies depending on the type of aromatic hydrocarbon, but is preferably 1 to 3, more preferably 2 to 3, and particularly preferably 2. Furthermore, the aromatic hydrocarbon having at least one sulfonic acid group may be in the form of a hydrate. The sulfonic acid group in the aromatic hydrocarbon having at least one sulfonic acid group may be in the form of a salt, and in this case, the form of the salt is not particularly limited, and examples thereof include a sodium salt, a potassium salt, an ammonium salt, a methylamine salt, an ethylamine salt, a diethylamine salt, a triethylamine salt, a monoethanolamine salt, and halides such as a chloride. The salt is preferably a sodium salt or a potassium salt, more preferably a sodium salt. Specific examples of the aromatic hydrocarbon having at least one sulfonic acid group include benzenesulfonic acid, 1,2-benzenedisulfonic acid, 1,3-benzenedisulfonic acid, 1,4-benzenedisulfonic acid, 1,2,4-benzenetrisulfonic acid, 1,3,5-benzenetrisulfonic acid, 1-naphthalenesulfonic acid, 2-naphthalenesulfonic acid, naphthalene-1,5-disulfonic acid, naphthalene-2,7-disulfonic acid, naphthalene-1,3,5-trisulfonic acid, naphthalene-1,3,6-trisulfonic acid, anthracene-1-sulfonic acid, anthracene-2-sulfonic acid, anthracene-3-sulfonic acid, and anthracene-1,3,6-trisulfonic acid.

Examples of the disaccharide used as the light-scattering adjustment reagent include, but are not limited to, sucrose, maltose, isomaltose, lactose, trehalose, sucralose, cellobiose, lactulose, turanose, galactosucrose, trehalosamine, maltitol, and lactitol. As the disaccharide, anon-reducing saccharide such as sucrose, trehalose, sucralose, galactosucrose, trehalosamine, maltitol, and lactitol is preferable, and trehalose and/or sucralose are more preferably used. In particular, sucralose having a low osmotic pressure is preferable because it has a large effect of suppressing the shrinkage of erythrocytes and can be dissolved in a large amount in an analysis sample.

Among these light-scattering adjustment reagents, an aromatic hydrocarbon having at least one sulfonic acid group or a salt thereof is preferable. More preferably, the light-scattering adjustment reagent is selected from the group consisting of 1,2-benzenedisulfonic acid, 1,3-benzenedisulfonic acid and 1,4-benzenedisulfonic acid, and their sodium and potassium salts. Even more preferably, the aromatic hydrocarbon having at least one sulfonic acid group is selected from sodium benzenesulfonate (BS) (see structural formula (1) below), disodium 1,3-benzenedisulfonate (DSB) (see structural formula (2) below), trisodium 1,3,5-benzenetrisulfonate (see structural formula (3) below), trisodium naphthalene-1,3,6-trisulfonate (TSN) (see structural formula (4) below), trisodium anthracene-1,3,6-trisulfonate (see structural formula (5) below), and hydrates thereof. Particularly preferably, disodium 1,3-benzenedisulfonate (DSB) and trisodium naphthalene-1,3,6-trisulfonate (TSN) are used as the light-scattering adjustment reagent. These light-scattering adjustment reagents can appropriately control the shrinkage of erythrocytes. That is, the change in scattered light before and after mixing of the specimen and the analyte concentration measuring reagent can be made to be the same degree (the average transmittance difference can be made smaller). In addition, because these light-scattering adjustment reagents are excellent in blood solubility, they can not only suppress undissolved residue in an analysis sample but also have good solubility in a blood sample having a low plasma volume and a high hematocrit value. Therefore, the scattered light and the measurement of the analyte are not affected. Therefore, the analyte can be measured with higher accuracy. These light-scattering adjustment reagents may be used alone or in combination of two or more kinds thereof.

[Chem. 7]

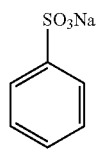

Structural formula (1)

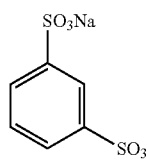

Structural formula (2)

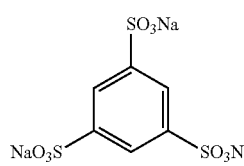

Structural formula (3)

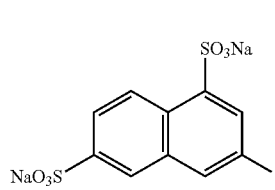

Structural formula (4)

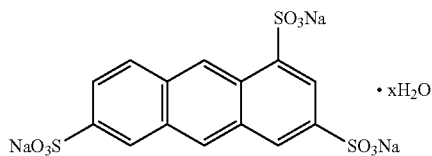

Structural formula (5)

The amount of the light-scattering adjustment reagent mixed with the specimen is not particularly limited as long as the scattered light can be made substantially the same before and after the analyte concentration measuring reagent is mixed, but the amount (concentration) of the light-scattering adjustment reagent in the aqueous fraction of the specimen is, for example, 0.5 to 215 mM, preferably 1 to 150 mM, more preferably 2 to 60 mM, and particularly preferably more than 3 mM and less than 40 mM. The mixing amount of the light-scattering adjustment reagent is particularly effective when the specimen is a whole blood sample having a hematocrit value of 20 to 60. With such an amount, the scattered light after mixing the reagent can be more effectively suppressed, and the analyte can be detected with higher accuracy. The amount of each component constituting the analyte concentration measuring reagent such as the light-scattering adjustment reagent is a value obtained by the following calculation method.

(Method for Measuring Amounts of Components Constituting Analyte Concentration Measuring Reagent)

In the present specification, the amount of each component constituting the reagent (the coloring reagent, the oxidoreductase, the light-scattering adjustment reagent, and other substances (for example, a transition metal compound) that may be optionally used) is measured according to the following method. Specifically, for example, a blood glucose level detection chip as described in Examples is produced using an analyte concentration measuring reagent. Add 1000 µL of RO water (glucose concentration 0 mg/1000 µL) into the chip to completely dissolve (elute) the analyte concentration measuring reagent (sample). The concentration of the coloring reagent in the sample is measured by UPLC (Ultra Performance Liquid Chromatograph SHIMADZU NEXERA X2, manufactured by Shimadzu Corporation). Based on the mass (mg) of the coloring reagent applied to each chip, the concentration of the coloring reagent when the RO water flows into the reagent part space and dissolves is calculated. For each component other than the chromogenic indicator, the concentration of each component when the RO water flows into the reagent part space and fills the reagent part space volume (that is, when the RO water is dissolved) is calculated based on the composition of the analyte concentration measuring reagent (concentration ratio of each component).

The amount (concentration) constituting the reagent is an amount (concentration) in a medium in which the reagent is dissolved, and is a value on the assumption that the specimen is entirely liquid (aqueous fraction). For example, when the specimen is a blood sample, the aqueous fraction is an extracellular fluid of erythrocyte excluding erythrocytes. Therefore, it is necessary to convert the amount (concentration) of each component into a numerical value in the extracellular fluid of erythrocyte in consideration of the hematocrit value of the blood sample. For example, when the concentration of the light-scattering adjustment reagent in a blood sample (specimen) having a hematocrit value of 40 is measured to be A (mM) by the above method, the mixing amount (concentration) of the light-scattering adjustment reagent is A×5/3 (=A/(1−0.4)) (mM).

In the present invention, it is also effective to appropriately select the coloring reagent from the viewpoint of more effectively suppressing the scattered light after mixing the reagent. To be more specific, the coloring reagent is preferably a 2-substituted benzothiazolyl-3-substituted phenyl-5-substituted sulfophenyl-2H-tetrazolium salt represented by the following formula (2):

[Chem. 8]

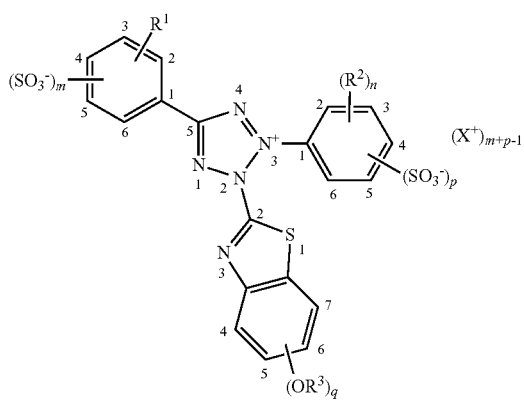

As will be described in detail below, in the analyte concentration measuring reagent according to the second aspect of the present invention and the chip according to the third aspect of the present invention, the coloring reagent is preferably a 2-substituted benzothiazolyl-3-substituted phenyl-5-substituted sulfophenyl-2H-tetrazolium salt represented by the above formula (2). In the present specification, the 2-substituted benzothiazolyl-3-substituted phenyl-5-substituted sulfophenyl-2H-tetrazolium salt represented by the above formula (2) is also simply referred to as "tetrazolium salt according to the present invention" or "tetrazolium salt".

The formazan compound produced from the tetrazolium salt according to the present invention has a maximum absorption wavelength in a wavelength region (600 nm or more, particularly 630 nm or more) that does not overlap with the absorption band of blood. Therefore, by using the tetrazolium salt according to the present invention, noise derived from a specimen can be reduced. That is, a signal relating to a biological component can be detected with high sensitivity. Specifically, in the tetrazolium salt according to the present invention, the benzothiazolyl group at the 2-position of the tetrazole skeleton is substituted with an alkoxy group. Therefore, for example, when a transition metal compound is further used, the maximum absorption wavelength of formazan generated from a tetrazolium salt or a chelate compound of formazan and a transition metal ion can be shifted to the longer wavelength side. Further, owing to the benzothiazolyl group present at the 2-position of the tetrazole ring, the formazan produced from the tetrazolium salt according to the present invention can efficiently and rapidly form a chelate compound with a transition metal ion such as $Co^{2+}$ or $Ni^{2+}$. This is believed to be due to the nitrogen atom of the benzothiazolyl group. Here, when the benzothiazolyl group is substituted with an alkoxy group, the electron density of the benzothiazolyl group is increased because the alkoxy group is electron-donating, and the formation of a chelate compound between formazan and a transition metal ion is considered to be performed more rapidly. Therefore, introduction of an alkoxy group onto the benzothiazolyl group present at the 2-position of the tetrazole ring can shift the maximum absorption wavelength to the longer wavelength side while maintaining the chelating ability of the formazan produced from the tetrazolium salt with the transition metal compound. Thus, according to the tetrazolium salt of the present invention, the maximum absorption wavelength of the formazan compound produced from the tetrazolium salt of the present invention can be further shifted to a wavelength region (600 nm or more, particularly 630 nm or more) that does not overlap with the main absorption band of hemoglobin. For this reason, it is possible to measure the concentration of a biological component in a wavelength region (600 nm or more) in which the maximum absorption wavelength does not overlap with the main absorption band of hemoglobin, and by using the tetrazolium salt according to the present invention, even the concentration of a biological component in a whole blood sample can be accurately measured.

Furthermore, in the tetrazolium salt according to the present invention, the phenyl group at the 5-position of the tetrazole skeleton has one or two sulfo groups (—$SO_3^-$), and the phenyl group at the 3-position of the tetrazole skeleton has zero or one sulfo group (—$SO_3^-$). Therefore, the tetrazolium salt has 1 to 3 sulfo groups (—$SO_3^-$) in the compound. Thus, the tetrazolium salt is excellent in water solubility and blood solubility. Further, the tetrazolium salt according to the present invention is excellent in stability.

Therefore, by using the tetrazolium salt according to the present invention, the concentration of a biological component can be measured sensitively and rapidly. Further, by using the tetrazolium salt according to the present invention, the concentration of a biological component can be measured with high sensitivity even after long-term storage. It should be noted that the above-described mechanism is a presumption and does not limit the technical scope of the present invention.

The tetrazolium salt according to the present invention has a structure of the following formula (2).

[Chem. 9]

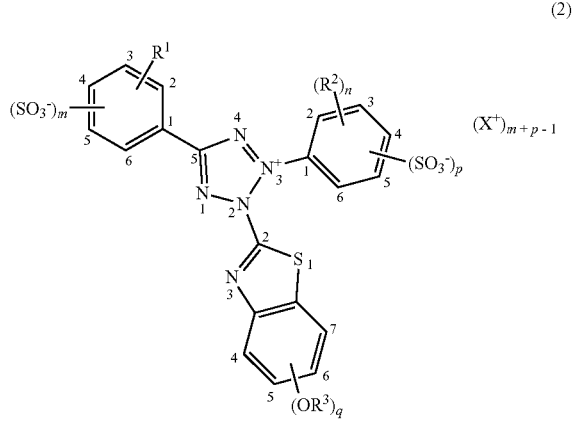

In the above formula (2), a substituted benzothiazolyl group is present at the 2-position of the tetrazole skeleton. In the above formula (2), the presence of the benzothiazolyl group at the 2-position of the tetrazole ring makes it possible to efficiently and rapidly form a chelate compound with the transition metal compound (the maximum absorption wavelength of the formazan compound can be shifted to a long wavelength region), for example, when the transition metal compound is further used. When at least one methoxy group or ethoxy group ($-OR^3$) is introduced into the benzothiazolyl group at the 2-position of the tetrazole skeleton, the maximum absorption wavelength at the time of chelation of the generated formazan with a transition metal ion such as $Ni^{2+}$ is further shifted to the longer wavelength side.

Here, q is 1 or 2, preferably 1. Here, when q is 1, $R^3$ is a methyl group or an ethyl group, and is preferably a methyl group from the viewpoint of water solubility. When $R^3$ is an alkyl group having 3 or more carbon atoms, the tetrazolium salt and the formazan produced from the tetrazolium salt are poor in water solubility, which is not preferred.

In the formula (2), from the viewpoint of the effect of shifting the maximum absorption wavelength to the longer wavelength side at the time of chelation with a transition metal ion such as $Ni^{2+}$, it is preferable that at least one $-OR^3$ of the substituted benzothiazolyl group present at the 2-position of the tetrazole skeleton is bonded to the 6-position of the benzothiazolyl group.

When q is 1, the substitution position of $-OR^3$, which is a substituent of the benzothiazolyl group present at the 2-position of the tetrazole skeleton, is not particularly limited, and may be any of 4-position, 5-position, 6-position, or 7-position. From the viewpoint of the effect of shifting the maximum absorption wavelength to the longer wavelength side at the time of chelation with a transition metal ion such as $Ni^{2+}$, the substitution position of $-OR^3$ is preferably bonded to the 6-position of the benzothiazolyl group.

When q is 2, $R^3$ is a hydrogen atom, a methyl group or an ethyl group, and at least one $R^3$ is a methyl group or an ethyl group. In addition, when q is 2, each $OR^3$ may be disposed adjacent to each other, and each $OR^3$ may form a ring with each other. In this case, as a preferable combination, $R^3$ is a combination of a hydrogen atom and a methyl group, or a combination of a methyl group and a methyl group. When q is 2, the substitution position of $-OR^3$, which is a substituent of the benzothiazolyl group present at the 2-position of the tetrazole skeleton, is not particularly limited as long as the two $-OR^3$ groups are disposed adjacent to each other, and may be any of 4,5-position, 5,6-position, or 6,7-position. From the viewpoint of the effect of shifting the maximum absorption wavelength to the longer wavelength side at the time of chelation with a transition metal ion such as $Ni^2$, the substitution position of at least one $-OR^3$ is preferably bonded to the 6-position of the benzothiazolyl group, that is, the substitution position of the two $-OR^3$ groups is preferably the 5,6-position or the 6,7-position. Specifically, when q is 2, the substituted benzothiazolyl group present at the 2-position of the tetrazole skeleton is preferably any of the following substituents.

[Chem. 10]

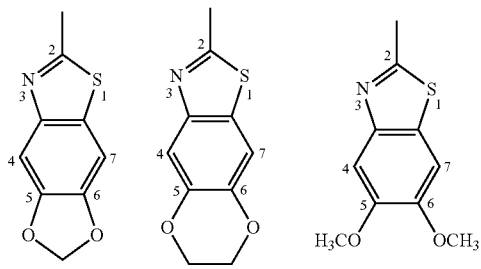

Further, when q is 2 and the substituted benzothiazolyl group present at the 2-position of the tetrazole skeleton is any one of the above substituents, the substituted sulfophenyl group present at the 3-position of the tetrazole skeleton is preferably a 4-methoxy-5-sulfophenyl group from the viewpoint of the effect of shifting the maximum absorption wavelength to the longer wavelength side at the time of chelation with a transition metal ion such as $Ni^2$.

In the formula (2), a substituted sulfophenyl group is present at the 5-position of the tetrazole skeleton. $R^1$ as a substituent of the sulfophenyl group is any one selected from the group consisting of a hydrogen atom, a hydroxy group, a methoxy group, and an ethoxy group. From the viewpoint of improving the water solubility of the tetrazolium salt and the formazan produced from the tetrazolium salt, $R^1$ is preferably a hydrogen atom or a hydroxy group, and from the viewpoint of stably forming a chelate with a transition metal ion in a wide pH range, $R^1$ is more preferably a hydrogen atom. When $R^1$ is a hydroxy group, a methoxy group, or an ethoxy group, the substitution position is not particularly limited, but is preferably the 4-position.

At least one sulfo group ($-SO_3^-$) is present at the 5-position of the tetrazole skeleton (m=1 or 2). This is considered to improve the water solubility and blood solubility of the tetrazolium salt and the formazan produced from the tetrazolium salt. In the formula (2), m is the number of the sulfo group ($-SO_3^-$) bonded to the phenyl group at the 5-position of the tetrazole skeleton, and is 1 or 2. In particular, when the sulfo group is at the 2- or 4-position, and further when the sulfo group is at the 2,4-position, the water solubility can be further improved. Furthermore, when the sulfo group is present at the 2,4-position, it is advantageous in that synthesis of a building block for synthesis is easy. From the viewpoint of high water solubility and stable formation of a chelate compound with a transition metal ion in a wide pH range or improvement of water solubility, m is preferably 2, and more preferably m is 2 and R is a hydrogen atom.

When m is 2, p, which is the number of the sulfo group ($-SO_3^-$) bonded to the phenyl group at the 3-position of the tetrazole skeleton, is preferably 1. By selecting the number of such substituents, the water solubility and blood solubility of the tetrazolium salt and the formazan produced therefrom are further improved.

From the viewpoint of the water solubility and blood solubility, it is preferable to satisfy any one of the following (1) to (4): (1) m=2 and p=1; (2) m=1 and n=0; (3) in the phenyl group present at the 5-position of the tetrazole skeleton, $R^1$ is a hydroxy group, and in this case the sulfo group ($-SO_3^-$) and the hydroxy group are at the 2,4-position or the 4,6-position; and (4) p=0 and at least one $R^2$ is a carboxyl group, and (1) m=2 and p=1 or (4) p=0 and at least one $R^2$ is a carboxyl group is more preferable. In addition, in the above (3), because the sulfo group ($-SO_3^-$) and the hydroxy group do not exist as adjacent substituents on the benzene ring, hydrogen bonding does not occur or is small, and thus both substituents can efficiently contribute to water solubility.

Here, the bonding position of the sulfo group ($-SO_3^-$) to the phenyl group present at the 5-position of the tetrazole skeleton is not particularly limited. When m is 2, the sulfo group ($-SO_3^-$) is preferably present at the 2,4- or 3,5-position of the phenyl group from the viewpoint of further improving the water solubility of the tetrazolium salt and the formazan produced from the tetrazolium salt, and shifting the maximum absorption wavelength to the longer wavelength side. The sulfo group is particularly preferably present at the 2,4-position of the phenyl group, and a tetrazolium salt compound that does not precipitate even in the presence of a high concentration of a transition metal ion can be obtained. That is, by using this tetrazolium salt as a coloring reagent, a quantifiable biological component-measuring reagent composition can be prepared even when the biological component is in a high concentration. That is, in a preferred embodiment of the present invention, the phenyl group at the 5-position of the tetrazole skeleton is preferably a phenyl group having a sulfo group ($-SO_3^-$) present at the 2,4-position.

In the formula (2), a substituted phenyl group is present at the 3-position of the tetrazole skeleton. Because the phenyl group is essentially substituted, n+p is 1 or more.

$R^2$ as a substituent of the phenyl group at the 3-position of the tetrazole skeleton is any one selected from the group consisting of a nitro group, $-OR^4$, and a carboxyl group. $R^2$ is preferably a nitro group or $-OR^4$ from the viewpoint of chelating ability between formazan and a transition metal ion, and is preferably a carboxyl group from the viewpoint of water solubility and blood solubility. Further, n is the number of $R^2$ bonded to the phenyl group at the 3-position of the tetrazole skeleton, and is an integer of 0 to 2. As described below, by introducing $R^2$, it is possible to shift the maximum absorption wavelength of the compound to a long wavelength region or to improve the stability of the compound, and thus n is preferably 1 or 2, and more preferably n is 1. When two $R^2$ are present, i.e., n is 2, $R^2$ may be the same or different.

When n is 1 or 2, it is preferred that at least one $R^2$ is a $-OR^4$ group. Thus, in a preferred embodiment of the present invention, n is 1 or 2 and at least one $R^2$ is a $-OR^4$ group. By introducing an alkoxy group as a substituent of the phenyl group, the stability of the compound is improved. From the viewpoint of improving the water solubility and blood solubility of the tetrazolium salt and the formazan produced from the tetrazolium salt, the $-OR^4$ group is preferably a methoxy group. Here, $R^4$ is a methyl group or an ethyl group, and is preferably a methyl group from the viewpoint of water solubility and blood solubility. When $R^4$ is an alkyl group having 3 or more carbon atoms, the tetrazolium salt and the formazan produced from the tetrazolium salt are poor in water solubility and blood solubility, which is not preferred.

When n is 1 or 2, the substitution position of $R^2$ is not particularly limited, but it is preferably the 2-, 3-, 4-, 5-, or 6-position of the substituted sulfophenyl group present at the 3-position of the tetrazole skeleton, and at least one $R^2$ is preferably at the 2- or 4-position, and more preferably at the 2- and/or 4-position. With such a structure, the water solubility and blood solubility are improved, and stability of the tetrazolium salt and the formazan produced from the tetrazolium salt can be improved.

p is the number of the sulfo group ($-SO_3^-$) bonded to the phenyl group at the 3-position of the tetrazole skeleton, and is 0 or 1. From the viewpoint of improving the water solubility and blood solubility of the tetrazolium salt and the formazan produced from the tetrazolium salt, p is preferably 1. When p is 1, because the sulfo group is an electron-withdrawing group, the presence of another electron-withdrawing group (for example, a nitro group) may destabilize the cationic charge of the nitrogen atom on the tetrazolium ring and reduce the stability of the compound. As described above, the stability of the compound is improved by introducing an alkoxy group as a substituent of a phenyl group, but when a nitro group is simultaneously introduced, the improvement of the stability by the introduction of an alkoxy group may not be exhibited. Therefore, from the viewpoint of improving stability, when p is 1, n is 1 or 2, preferably n is 1 and $R^2$ is preferably any one selected from the group consisting of $-OR^4$ and a carboxyl group, and $R^2$ is more preferably $-OR^4$. Alternatively, from the viewpoint of improving the water solubility and blood solubility of the tetrazolium salt and the formazan produced from the tetrazolium salt, it is preferable that p is 0 and at least one $R^2$ is a carboxyl group. That is, in a preferred embodiment, in the formula (2), p is 1, or p is 0 and at least one $R^2$ is a carboxyl group. More preferably, m is 2 and p is 1, or p is 0 and at least one $R^2$ is a carboxyl group.

When p is 1, the substitution position of the sulfo group ($-SO_3^-$) substituting the phenyl group at the 3-position of the tetrazole skeleton is not particularly limited, but is preferably the 3- or 5-position, and more preferably the 3-position. By substituting this position with a sulfo group, the stability of the tetrazolium salt and the formazan produced from the tetrazolium salt can be more effectively improved.

Further, in the formula (2), the substituent present at the 3-position of the tetrazole skeleton is preferably a 4-methoxy-3-sulfophenyl group, a 2-methoxy-5-sulfophenyl group, a 2-methoxy-4-nitro-5-sulfophenyl group, a 2-methoxy-4-nitrophenyl group, a 4-sulfophenyl group, a 4-carboxy-2-methoxyphenyl group, a 5-carboxy-2-methoxyphenyl group, a 3-carboxy-4-methoxyphenyl group, or a 4-methoxy-5-sulfophenyl group, more preferably a 4-methoxy-3-sulfophenyl group, a 2-methoxy-5-sulfophenyl group, a 3-carboxy-4-methoxyphenyl group, or a 4-methoxy-5-sulfophenyl group, and particularly preferably a 4-methoxy-3-sulfophenyl group, a 4-methoxy-5-sulfophenyl group, or a 2-methoxy-5-sulfophenyl group. With such a structure, the coloring sensitivity is improved, the water solubility and blood solubility are improved, and stability of the tetrazolium salt and the formazan produced from the tetrazolium salt can be improved. In addition, it is particularly preferable that the phenyl group present at the 3-position of the tetrazole skeleton is a 4-methoxy-3-sulfophenyl group because the maximum absorption wavelength of the formazan compound itself can be set to a longer wavelength region.

The total number (m+p) of sulfo groups present in the formula (2) is preferably 2 or more, and more preferably 3, from the viewpoint of improving the water solubility of the tetrazolium salt and the formazan produced from the tetrazolium salt.

In the above formula (2), X represents a hydrogen atom or an alkali metal. Here, X is present to neutralize the anion (sulfo group ($-SO_3^-$)). Therefore, the type of the alkali metal is not particularly limited, and may be any of lithium, sodium, potassium, rubidium, and cesium.

Preferred examples of tetrazolium salts include the following. In the following structures, X represents an alkali metal.

[Chem. 11]
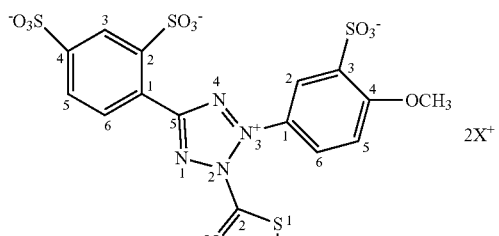 2X⁺
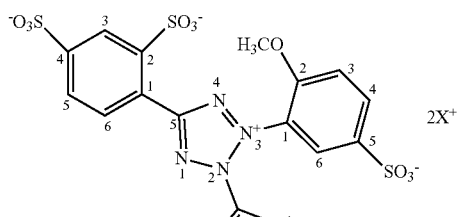 2X⁺
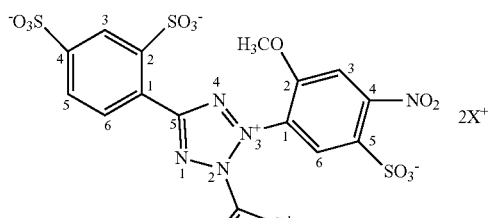 2X⁺
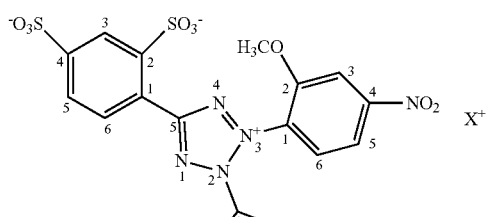 X⁺
[Chem. 12]
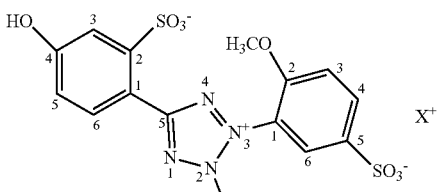 X⁺
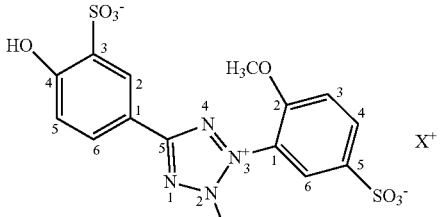 X⁺
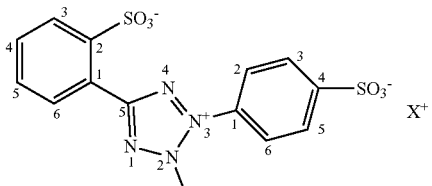 X⁺
[Chem. 13]
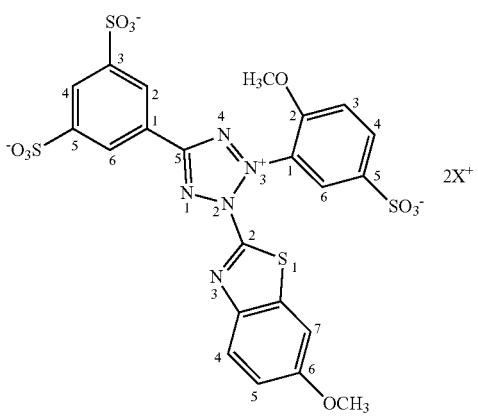 2X⁺

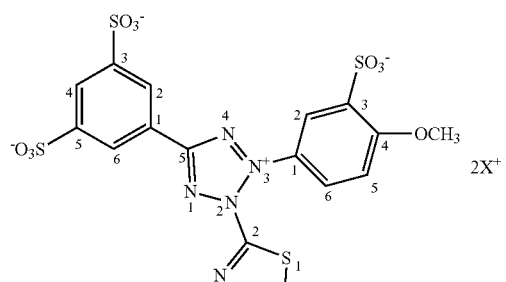
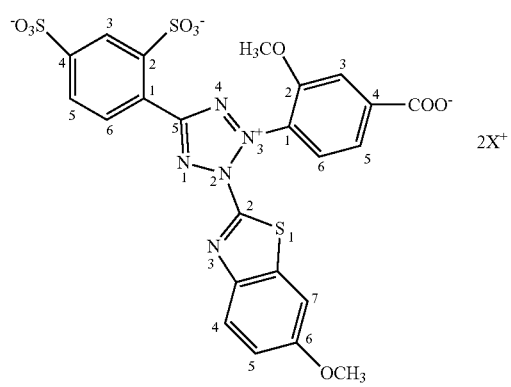
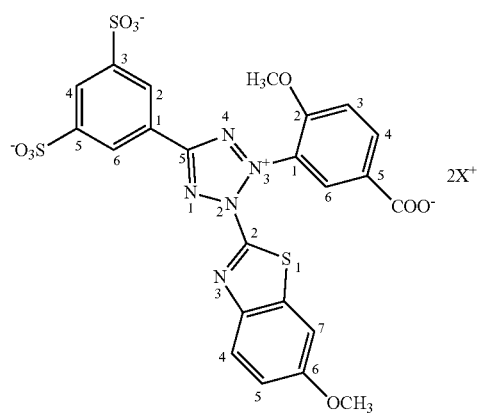
[Chem. 14]
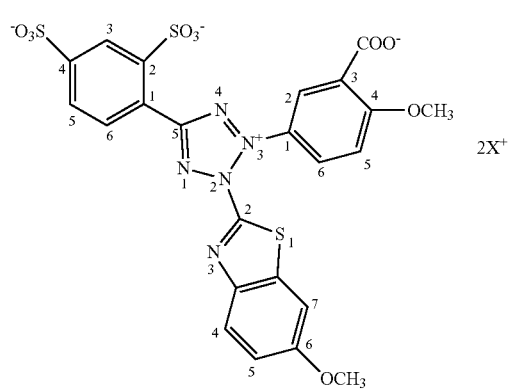
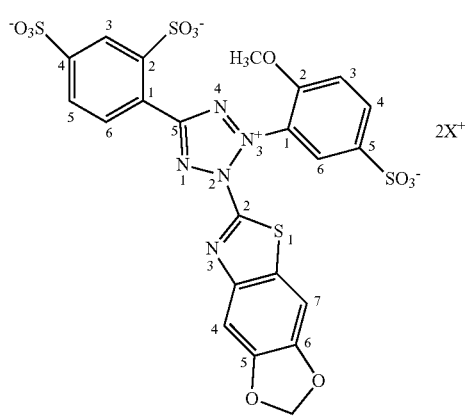
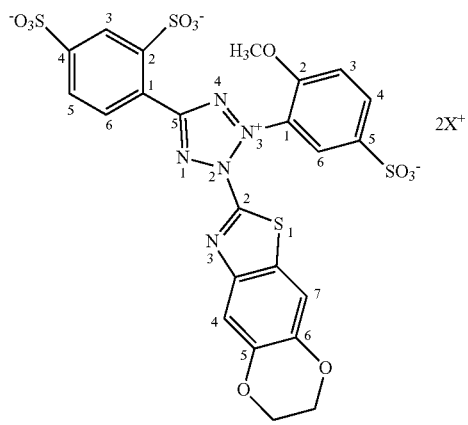
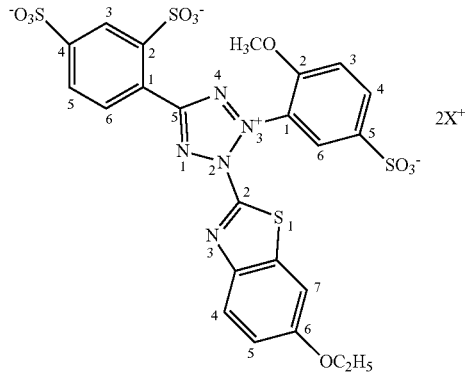
[Chem. 15]
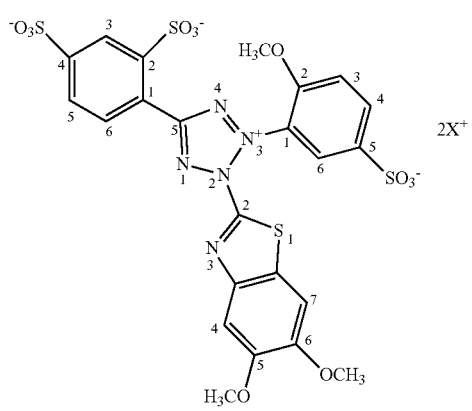

-continued

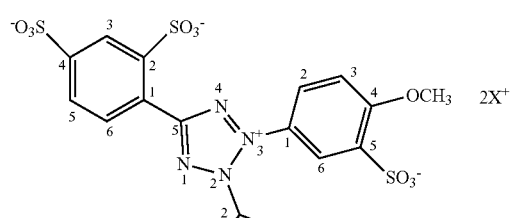

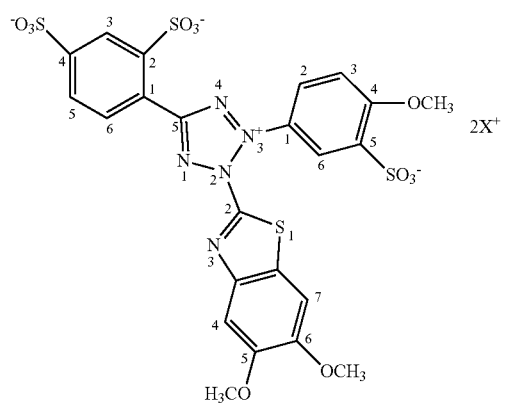

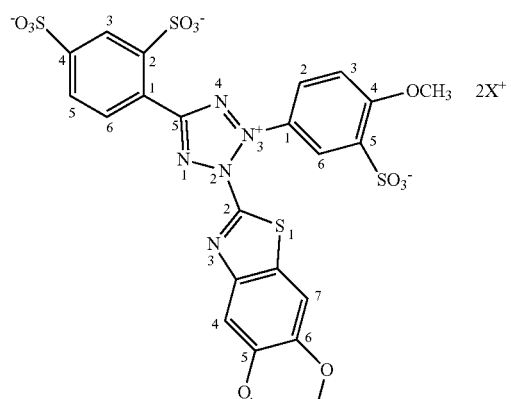

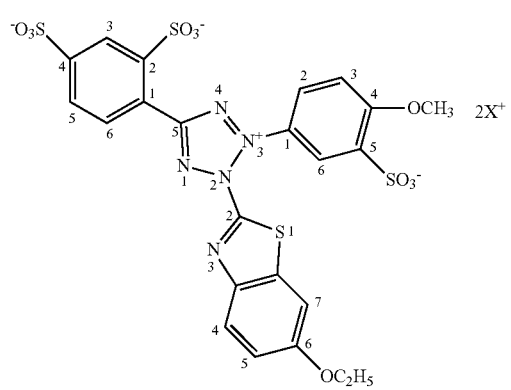

The method for producing the tetrazolium salt according to the present invention is not particularly limited, and conventionally known methods can be applied in the same manner or with appropriate modification. For example, hydrazone is synthesized by dehydration condensation of aldehyde and hydrazine, and then the corresponding diazonium salt is reacted in an aqueous solvent under basic conditions to obtain formazan. As the basifying agent, sodium hydroxide, potassium hydroxide or the like is used. The resulting formazan can then be oxidized in an alcohol solvent (e.g., methanol, ethanol) using an oxidizing agent such as ethyl nitrite, butylnitrite, or sodium hypochlorite to provide the tetrazolium salt of the formula (2). In one embodiment, a hydrazino substituted benzothiazole having the following structure:

[Chem. 16]

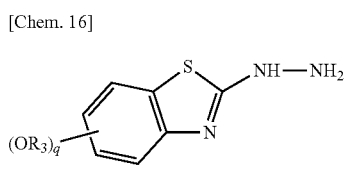

is reacted with a substituted sulfonated benzaldehyde having the following structure:

[Chem. 17]

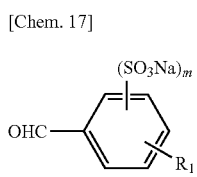

to obtain a hydrazone compound having the following structure:

[Chem. 18]

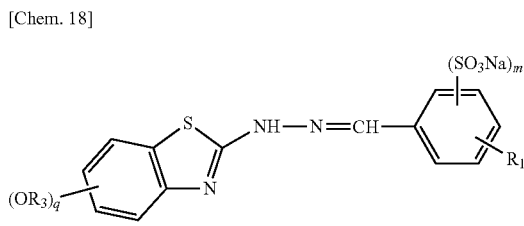

On the other hand, hydrochloric acid is added to a substituted sulfoaniline having the following structure while cooling with ice,

[Chem. 19]

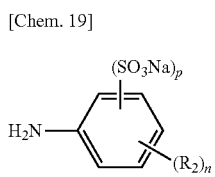

and a sodium nitrite solution is further added dropwise to obtain a benzenediazonium chloride compound having the following structure:

[Chem. 20]

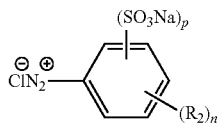

The hydrazone compound obtained above is reacted with a benzenediazonium chloride compound under basic conditions (for example, in the presence of sodium hydroxide or potassium hydroxide) to obtain a formazan compound having the following structure:

[Chem. 21]

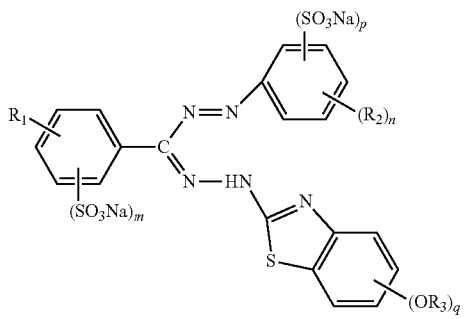

Then, the formazan compound thus obtained is oxidized with an oxidizing agent (e.g., a nitrite such as sodium nitrite, ethyl nitrite, or butyl nitrite) in an alcohol solvent (e.g., methanol or ethanol) to provide the tetrazolium salt of the present invention.

The formazan produced from the tetrazolium salt according to the present invention or the chelate compound of formazan and a transition metal ion (when a transition metal compound is further used) has a maximum absorption wavelength in a wavelength region (600 nm or more, particularly 650 nm or more) that does not overlap with the main absorption band of hemoglobin, either alone or by forming a chelate compound with a transition metal compound. Further, the tetrazolium salt according to the present invention has high water solubility. Therefore, by using the tetrazolium salt according to the present invention, the concentration of a biological component can be measured with high sensitivity even for a specimen, particularly a whole blood sample. Specifically, the maximum absorption wavelength ($\lambda$max) of the formazan produced from the tetrazolium salt according to the present invention or the chelate compound of formazan and a transition metal ion is preferably 600 nm or more, more preferably 630 nm or more, and particularly preferably 650 nm or more. Formazan or a chelate compound of formazan and a transition metal ion having such a maximum absorption wavelength (therefore, a tetrazolium salt capable of forming such formazan) is hardly affected by absorption of blood, and the concentration of a biological component can be measured more accurately and with good sensitivity. The upper limit of the maximum absorption wavelength ($\lambda$max) of the formazan produced from the tetrazolium salt according to the present invention or the chelate compound of formazan and a transition metal ion is not particularly limited, but is usually 900 nm or less, preferably 800 nm or less. In the present specification, the maximum absorption wavelength ($\lambda$max) is a value measured according to the following method.

(Evaluation of Maximum Absorption Wavelength ($\lambda$max))

A 10 mM MOPS aqueous solution is added so that the final concentrations of the respective formazan compounds are 50 to 200 mM to prepare 100 µL of each sample. Separately, a 1M nickel ion aqueous solution is prepared. To 100 µL of the sample, 10 µL of the 1M nickel ion aqueous solution is added, and the mixture is rapidly stirred to prepare a mixed solution. The spectrum of the mixed solution is measured with a spectrophotometer (measurement cell length: 10 mm) (n=1). Based on each spectrum, the maximum absorption wavelength ($\lambda$max) (nm) of each compound in formazan is determined.

The amount of the coloring reagent (particularly, the tetrazolium salt of the formula (2)) to be mixed with the specimen is not particularly limited as long as the concentration of the desired analyte (biological component) can be measured, but it is preferable that the tetrazolium salt is contained in an amount sufficient for the amount of the desired analyte present. In view of the above viewpoint and the concentration of a biological component to be usually measured, the amount (concentration) of the coloring reagent in the aqueous fraction of the specimen is, for example, preferably 10 to 150 mM, more preferably more than 10 mM and less than 130 mM. The mixing amount of the coloring reagent is particularly effective when the specimen is a whole blood sample having a hematocrit value of 20 to 60. In such an amount, the coloring reagent reacts according to the amount of substantially all (for example, 95% by mol or more, preferably 98% by mol or more, particularly preferably 100% by mol) of the analyte (biological component) contained in the specimen. When the amount is within the above range, the coloring reagent is substantially completely dissolved in the specimen. For this reason, because scattering due to insoluble matter is suppressed, measurement accuracy can be improved. Therefore, the concentration of the desired biological component can be measured accurately and quickly with good sensitivity.

In addition, the oxidoreductase that can be used in the present invention is not particularly limited, and may be appropriately selected according to the type of a biological component to be measured. Specific examples thereof include glucose dehydrogenase (GDH) such as glucose dehydrogenase (GDH), glucose dehydrogenase (PQQ-GDH) using pyrroloquinoline quinone (PQQ) as a coenzyme, glucose dehydrogenase (GDH-FAD) using flavin adenine dinucleotide (FAD) as a coenzyme, glucose dehydrogenase (GDH-NAD) using nicotinamide adenine dinucleotide (NAD) as a coenzyme, and glucose dehydrogenase (GDH-NADP) using nicotine adenine dinucleotide phosphate (NADP) as a coenzyme, glucose oxidase (GOD), lactate dehydrogenase (LDH), cholesterol dehydrogenase, and urate dehydrogenase. Here, the oxidoreductase may be used alone or in combination of two or more kinds thereof. For example, when the biological component is glucose, the oxidoreductase is preferably glucose dehydrogenase or glucose oxidase. When the biological component is cholesterol, the oxidoreductase is preferably cholesterol dehydrogenase or cholesterol oxidase.

The amount of the oxidoreductase to be mixed with the specimen is not particularly limited, and can be appropriately set according to the types of the enzyme and the coloring reagent to be used and the range of the target analyte. The mixing amount of the oxidoreductase is, for example, 0.20 to 1.0 mol, preferably 0.3 to 0.8 mol, with respect to 1 mol of the coloring reagent. Alternatively, the mixed amount of the oxidoreductase may be an amount such that the concentration of the oxidoreductase in the analysis sample is, for example, 2 to 50 MU ($\times 10^6$ U)/L, preferably 3 to 35 MU/L. The mixing amount of the light-scattering adjustment reagent is particularly effective when the specimen is a whole blood sample having a hematocrit value of 20 to 60.

In this step, a coloring reagent, an oxidoreductase, and a light-scattering adjustment reagent may be mixed with the specimen prepared in the step (1), but it is preferable to further add a transition metal compound. By using the transition metal compound in combination with the light-scattering adjustment reagent, the scattered light in the specimen and the scattered light in the analysis sample can be made substantially the same. Here, the transition metal compound may be mixed together with the coloring reagent, the oxidoreductase, and the light-scattering adjustment reagent, or may be mixed before or after mixing with the coloring reagent, the oxidoreductase, and the light-scattering adjustment reagent. Preferably, the transition metal compound is mixed together with the coloring reagent, the oxidoreductase, and the light-scattering adjustment reagent.

The transition metal compound that can be used when the transition metal compound is mixed with the specimen in step (2) is not particularly limited as long as it forms a chelate compound with the coloring reagent (particularly, the tetrazolium salt of the formula (2)) in an ionic form. When the coloring reagent is the tetrazolium salt of the formula (2), the maximum absorption wavelength can further be shifted to the longer wavelength side by the chelate formation between the transition metal ion and the coloring reagent. For example, when the coloring reagent is the tetrazolium salt of the formula (2) and the transition metal ion is a nickel ion, the nickel ion and the tetrazolium salt of the formula (2) form a chelate compound at a molar ratio of 1:2 (molar ratio of nickel ion:tetrazolium salt of the formula (2)) in consideration of the structural formula. Further, even in the case of measuring the concentration of biological components in a specimen (whole blood sample), formazan has a maximum absorption wavelength in a wavelength region (600 nm or more) that does not overlap with the main absorption band of hemoglobin. Therefore, the measurement sensitivity of the concentration of the biological component can be further improved even for a specimen, particularly a whole blood sample. The transition metal compound that can be used when the analyte concentration measuring reagent contains a transition metal compound is not particularly limited. Specifically, compounds capable of generating transition metal ions such as nickel ions ($Ni^{2+}$), cobalt ions ($Co^{2+}$), zinc ions ($Zn^{2+}$), and copper ions ($Cu^{2+}$) can be used. Such ions can shift the maximum absorption wavelength of formazan to the longer wavelength side. Of these, nickel ions are preferred. Because nickel ions are not easily oxidized or reduced, measurement errors can be more effectively reduced. Thus, according to a preferred embodiment of the present invention, the transition metal compound is a nickel compound. The compound capable of generating a transition metal ion is not particularly limited, but is preferably a compound capable of generating an ion in an aqueous liquid (e.g., water, buffer solution, blood, body fluid). Examples thereof include chlorides, bromides, sulfates, and organic acid salts (e.g., gluconates, acetates, oxalates, and citrates) of the transition metals. The transition metal compound salt is preferably an organic acid salt of a transition metal. In this case, the influence on blood cells can be easily controlled. These transition metal compounds may be used alone or in combination of two or more kinds thereof.

In the above embodiment, the amount of the transition metal compound to be mixed with the specimen is not particularly limited as long as it is stoichiometrically larger than the amount capable of sufficiently forming a chelate compound with the coloring reagent, and may vary depending on the amount of the coloring reagent. For example, the amount of the transition metal compound is preferably 4.0 mol or more, more preferably more than 4.0 mol, particularly preferably 4.5 mol or more, with respect to 1 mol of the coloring reagent. That is, in a preferred embodiment of the present invention, in the step (2), the transition metal compound is mixed at a ratio of 4.0 mol or more with respect to 1 mol of the coloring reagent. As described in detail below, the analyte concentration measuring reagent according to the second aspect of the present invention preferably further contains a transition metal compound in an amount of 4.0 mol or more (more preferably more than 4.0 mol, particularly preferably 4.5 mol or more) with respect to 1 mol of the coloring reagent. Similarly, in the chip according to the third aspect of the present invention, the reaction unit preferably further contains a transition metal compound at a ratio of 4.0 mol or more (more preferably more than 4.0 mol, particularly preferably 4.5 mol or more) with respect to 1 mol of the coloring reagent. The amount of the transition metal compound is particularly effective when the coloring reagent is the tetrazolium salt of the formula (2). In addition, The mixing amount of the light-scattering adjustment reagent is particularly effective when the specimen is a whole blood sample having a hematocrit value of 20 to 60. With such an amount, the maximum absorption wavelength of the formazan compound can be shifted to a desired wavelength region. The upper limit of the mixed amount of the transition metal compound is not particularly limited, but is preferably 8 mol or less, more preferably 7 mol or less, with respect to 1 mol of the coloring reagent (particularly, 2-substituted benzothiazolyl-3-substituted phenyl-5-substituted sulfophenyl-2H-tetrazolium salt), in consideration of the effect of suppressing insoluble matter in an analysis sample.

In the above embodiment, from the viewpoint of more effectively suppressing the scattered light after mixing the reagent, it is also effective to appropriately adjust the mixing ratio of the light-scattering adjustment reagent and the transition metal compound. Specifically, the amount of the light-scattering adjustment reagent is preferably more than 0 mol and 0.24 mol or less, more preferably 0.03 to 0.12 mol, and particularly preferably 0.05 to 0.10 mol, with respect to 1 mol of the transition metal compound. That is, in a preferred embodiment of the present invention, in the step (2), the transition metal compound is further mixed with the specimen at a mixing ratio of the light-scattering adjustment reagent to the transition metal compound (mol of the light-scattering adjustment reagent to 1 mol of the transition metal compound) of more than 0 mol and 0.24 mol or less. In a more preferred embodiment of the present invention, in the step (2), the transition metal compound is further mixed with the specimen at a mixing ratio of the light-scattering adjustment reagent to the transition metal compound (defined as mol of the light-scattering adjustment reagent to 1 mol of the transition metal compound) of 0.03 to 0.12 mol. In a particularly preferred embodiment of the present invention, in the step (2), the transition metal compound is further mixed with the specimen at a mixing ratio of the light-scattering adjustment reagent to the transition metal compound (mol of the light-scattering adjustment reagent to 1 mol of the transition metal compound) of 0.05 to 0.10 mol. With such a mixing ratio, the change in the refractive index of the intracellular fluid of erythrocyte and the extracellular fluid of erythrocyte before and after mixing the reagent can be suppressed to a lower level, and as a result, the shrinkage of the erythrocytes can be more appropriately adjusted so that the amount of change in the refractive index of the intracellular fluid of erythrocyte ($\Delta n_{RBC} = n_{RBC\text{-}1} - n_{RBC\text{-}2}$) and the amount of change in the refractive index of the extracellular fluid of erythrocyte ($\Delta n_S = n_{S\text{-}1} - n_{S\text{-}2}$) before and after mixing the reagent are substantially the same. Therefore, the analyte concentration can be measured with higher accuracy.

In addition to the above, from the viewpoint of more effectively suppressing the scattered light after mixing the reagent, it is effective to appropriately adjust the total concentration of the light-scattering adjustment reagent and the transition metal compound. Specifically, the total concentration of the light-scattering adjustment reagent and the transition metal compound in the aqueous fraction of the specimen is preferably 810 mmol/L or less, more preferably 750 mmol/L or less, still more preferably 50 to 665 mmol/L, and particularly preferably more than 100 mmol/L and less than 665 mmol/L. By using such a small amount, the change in the refractive index of the intracellular fluid of erythrocyte and the extracellular fluid of erythrocyte before and after mixing the reagent can be suppressed to a lower level, and as a result, the shrinkage of the erythrocytes can be more appropriately adjusted so that the amount of change in the refractive index of the intracellular fluid of erythrocyte ($\Delta n_{RBC} = n_{RBC\text{-}1} - n_{RBC\text{-}2}$) and the amount of change in the refractive index of the extracellular fluid of erythrocyte ($\Delta n_S = n_{S\text{-}1} - n_{S\text{-}2}$) before and after mixing the reagent are substantially the same. Therefore, the analyte concentration can be measured with higher accuracy.

In this manner, an analysis sample is prepared. Here, the transmittance of the analysis sample is not limited as long as the scattered light is substantially the same as that of the specimen (the average transmittance difference from the specimen is more than −15.0% and less than 15.0%). For example, the transmittance of the analysis sample in the wavelength range of 800 nm to 950 nm is preferably less than 50%. In addition, in the wavelength region of 750 nm to 850 nm, the transmittance of the analysis sample is preferably lower than the transmittance of the specimen. In such a case, because the scattered light (transmittance) of the analysis sample can be measured in a state where the difference between the scattered light (transmittance) of the analysis sample and the scattered light (transmittance) of the specimen is small (the difference in average transmittance between the analysis sample and the specimen can be further reduced), the analysis accuracy can be improved.

As described above, the present invention is characterized in that an analysis sample having substantially the same scattered light as that of a specimen is obtained by combining a light-scattering adjustment reagent and a transition metal compound. In addition to the above, it is preferable to perform at least one of the following (a) to (c) from the viewpoint of more effectively suppressing scattered light after mixing the reagent.

(a) The 2-substituted benzothiazolyl-3-substituted phenyl-5-substituted sulfophenyl-2H-tetrazolium salt represented by the above formula (2) is used;

(b) in the step (2), the transition metal compound is further mixed with the specimen at a mixing ratio of the light-scattering adjustment reagent to the transition metal compound (defined as mol of the light-scattering adjustment reagent to 1 mol of the transition metal compound) of more than 0 mol and 0.24 mol or less (more preferably 0.03 to 0.12 mol, particularly preferably 0.05 to 0.10 mol); and (c) in the step (2), the transition metal compound is mixed at a ratio of 4.0 mol or more with respect to 1 mol of the coloring reagent. Of the above, it is preferred to perform at least (a), more preferred to perform (a) and (b) and/or (c), still more preferred to perform at least (a) and (b), and particularly preferred to perform all (a), (b) and (c).

In addition, when the above (b) is performed, the following (d) is preferably performed in combination.

(d) The total concentration of the light-scattering adjustment reagent and the transition metal compound is set to 750 mmol/L or less (more preferably 50 to 665 mmol/L, particularly preferably more than 100 mmol/L and less than 665 mmol/L).

[Step (3)]

In this step, the analyte concentration is measured using the analysis sample obtained in the step (2). Thus, the concentration of a specific analyte (biological component) contained in a specimen can be measured with high accuracy. Here, the measurement method is not particularly limited, and can be appropriately selected according to the type of the biological component to be measured. For example, when the biological component is β-D-glucose (BG) and the oxidoreductase is glucose dehydrogenase (GDH), glucose is oxidized by GDH to produce gluconic acid, which utilizes reduction of a coenzyme or an electron transfer agent of GDH. Specifically, the methods are roughly classified into a method (colorimetric method) of optically measuring the degree of changing color of a tetrazolium salt (hence formazan or a chelate compound of formazan and a transition metal ion) reduced as a result of electron transfer and a method (electrode method) of measuring a current generated by an oxidation-reduction reaction. Among the above-mentioned methods, the measurement of the blood glucose level by the colorimetric method has advantages in that correction using the hematocrit value is easily performed when the blood glucose level is calculated, the manufacturing process is simple, and the like. Therefore, the analyte concentration measuring reagent can be suitably used for the colorimetric method. In particular, when the glucose concentration in a whole blood sample is measured, the colorimetric method is preferably used, and it is particularly preferable to use the tetrazolium salt of the above formula (2) as a coloring reagent. However, even in the electrode method, measurement can be performed in a state where the difference between the analysis sample and the specimen is small.

<Analyte Concentration Measuring Reagent>

As described above, according to the method of the present invention, the analyte concentration can be measured with higher accuracy. Accordingly, in a second aspect of the present invention, there is provided an analyte concentration measuring reagent including a coloring reagent, an oxidoreductase, and a light-scattering adjustment reagent. Preferably, the analyte concentration measuring reagent of the present invention includes a coloring reagent, an oxidoreductase, a transition metal compound, and a light-scattering adjustment reagent. Here, because preferred forms (types, contents, mixing ratios, and the like) of the coloring reagent, the oxidoreductase, the transition metal compound, and the light-scattering adjustment reagent are the same as those in the first aspect, the description thereof is omitted here.

The analyte (biological component measurement target) is not particularly limited as long as it contains a target biological component. Specific examples thereof include blood and body fluids such as urine, saliva, and interstitial fluid as biological component measurement targets. In addition, the biological component is not particularly limited, and a biological component that is usually measured by a colorimetric method or an electrode method can be used in the same manner. Specific examples thereof include glucose, cholesterol, neutral fat, nicotinamide adenine dinucleotide phosphate (NADPH), nicotinamide adenine dinucleotide (NADH), and uric acid. That is, according to a preferred embodiment of the second aspect of the present invention, the analyte concentration measuring reagent of the present invention is used for measuring the concentrations of glucose, cholesterol, neutral fat, nicotinamide adenine dinucleotide phosphate (NADPH), nicotinamide adenine dinucleotide (NADH), and uric acid in blood or body fluids.

The use form of the analyte concentration measuring reagent of the present invention is not particularly limited, and may be any form of solid, gel, sol, or liquid. The analyte concentration measuring reagent of the present invention contains a coloring reagent, an oxidoreductase and a light-scattering adjustment reagent, and preferably contains a coloring reagent, an oxidoreductase, a transition metal compound and a light-scattering adjustment reagent, but may further contain other components in addition to the above components. Here, as the other component, a component that is appropriately selected according to the type of the biological component to be measured and is added to measure the concentration of the biological component can be used in the same manner. Specific examples thereof include an electron carrier, a buffer, a pH adjustor, a surfactant, and water (for example, RO water). Here, the above-mentioned other components may be used alone or in combination of two or more kinds thereof. In addition, each of the above-mentioned other components may be used alone or in combination of two or more kinds thereof.

The electron carrier is not particularly limited, and a known electron carrier may be used. Specific examples thereof include diaphorase, phenazine methosulfate (PMS), 1-methoxy-5-methylphenazinium methylsulfate (1-Methoxy PMS or m-PMS), nicotinamide adenine dinucleotide phosphate (NADPH), and nicotinamide adenine dinucleotide (NADH). The electron carrier is not necessarily contained, and the electron carrier may not be blended depending on the type of oxidoreductase used. The electron carrier may be used alone or in combination of two or more kinds thereof. When the analyte concentration measuring reagent contains an electron carrier, the content of the electron carrier is not particularly limited and can be appropriately selected depending on the amount of the coloring reagent. For example, the content of the electron carrier is preferably 0.05 to 10% by mass, and more preferably 0.1 to 5% by mass with respect to the coloring reagent. Such an amount allows the reduction reaction to proceed more efficiently. Here, for example, when the coloring reagent is the tetrazolium salt of the above formula (2), the biological component is β-D-glucose, the transition metal ion is nickel ion, the oxidoreductase is glucose dehydrogenase (GDH-FAD) using flavin adenine dinucleotide as a coenzyme, and the electron carrier is 1-methoxy-5-methylphenazium methyl sulfate (m-PMS), β-D-glucose and m-PMS are first subjected to the action of GDH-FAD to produce gluconic acid and reduced m-PMS, and from the reduced m-PMS and tetrazolium salt, m-PMS and formazan are produced to develop color. Further, the formazan forms a chelate compound with nickel ions, and the maximum absorption wavelength is shifted to the longer wavelength region side (for example, 600 nm or more). Therefore, by using the analyte concentration measuring reagent of the present invention, the influence of absorption of hemoglobin can be reduced, so that the concentration of a biological component can be measured with high sensitivity even for a specimen, particularly a whole blood sample.

The buffer is not particularly limited, and a buffer generally used for measuring the concentration of a biological component can be similarly used. Specifically, a phosphate buffer, a citrate buffer, a citrate-phosphate buffer, a trishydroxymethylaminomethane-HCl buffer (Tris-HCl buffer), an acetate buffer, Good buffers such as a MES buffer (2-morpholinoethanesulfonic acid buffer), a TES buffer (N-tris (hydroxymethyl) methyl-2-aminoethanesulfonic acid buffer), a MOPS buffer (3-morpholinopropanesulfonic acid buffer), a MOPS-NaOH buffer, a HEPES buffer (4-(2-hydroxyethyl)-1-piperazineethanesulfonic acid buffer), and a HEPES-NaOH buffer, amino acid-based buffers such as a glycine-hydrochloric acid buffer, a glycine-NaOH buffer, a glycylglycine-NaOH buffer, and a glycylglycine-KOH buffer, borate-based buffers such as a Tris-borate buffer, a borate-NaOH buffer, and a borate buffer, or an imidazole buffer may be used. Among these, a phosphate buffer, a citrate buffer, a citrate-phosphate buffer, a Tris-HCl buffer, a MES buffer, an acetate buffer, a MOPS buffer, and a HEPES-NaOH buffer are preferable. Here, the concentration of the buffer is not particularly limited, but is preferably 0.01 to 1.0 M. In the present invention, the concentration of the buffer means the concentration (M, mol/L) of the buffer contained in the aqueous solution. In addition, the pH of the buffer solution preferably has no effect on the biological component. From the above viewpoint, the pH of the buffer solution is preferably around neutral, for example, about 5.0 to 8.0.

The pH adjustor is also not particularly limited, and an acid (hydrochloric acid, sulfuric acid, phosphoric acid, or the like) or a base (potassium hydroxide, sodium hydroxide, potassium carbonate, sodium carbonate, or the like) is appropriately selected and used so as to have a pH generally applied when measuring the concentration of a biological component. The pH adjustor may be used as it is or in the form of an aqueous solution. The amount of the pH adjustor is not particularly limited, but is preferably an amount such that the pH of the reagent is around neutral, for example, about 5.0 to 8.0.

In addition, a solvent such as a surfactant or an alcohol can be appropriately added at the time of preparing the reagent according to the purpose.

<Analyte Concentration Measuring Chip>

The analyte concentration measuring reagent of the present invention may be used as it is for measuring the concentration of a biological component or may be incorporated into a chip for measuring the concentration of an analyte (biological component). That is, the present invention also provides a chip for measuring the analyte concentration in a specimen, the chip having a reaction unit, wherein the reaction unit contains a coloring reagent, an oxidoreductase, and a light-scattering adjustment reagent. Preferably, the reaction unit of the chip of the present invention contains a coloring reagent, an oxidoreductase, a transition metal compound, and a light-scattering adjustment reagent.

The analyte concentration measurement method and the measuring reagent of the present invention can be incorporated into an automatic analyzer, a measurement kit, a simple blood glucose meter, or the like, and used for routine clinical tests. The reagents of the present invention can also be incorporated into commercially available biosensors. When the analyte concentration measuring reagent is incorporated into a chip for measuring the concentration of an analyte (biological component), the content of the reagent per 1 chip is not particularly limited, and an amount commonly used in the art can be employed in the same manner, but it is preferable that the coloring reagent is contained in an amount sufficient for the amount of the desired biological component present. In view of the above viewpoint and the concentration of the biological components to be usually measured, the amount (concentration) of the coloring reagent (in particular, the tetrazolium salt of the formula (2)) per 1 chip is preferably 2.5 nmol or more, more preferably 3.0 to 50.0 nmol, and particularly preferably 5 to 30 nmol. In such an amount, the coloring reagent reacts according to the amount of substantially all the biological components contained in the specimen. Therefore, the concentration of the desired biological component can be measured accurately and quickly with good sensitivity.

Hereinafter, the form of the measuring chip (colorimetric blood glucose meter) of the present invention used for measuring a blood glucose level by a colorimetric method will be described with reference to the drawings. However, the present invention is characterized by using the method for measuring the concentration of the analyte (biological component) of the present invention and the reagent for the measurement, and the structure of the chip is not particularly limited. Therefore, the analyte concentration measuring reagent of the present invention may be applied to a commercially available measuring chip or a chip described in publications such as WO 2014/04970 and WO 2016/051930. Similarly, in the following embodiment, a specific form of a chip for measuring a blood glucose level will be described, but the measuring chip is not limited to this use, and can be applied to other uses in the same manner or with appropriate modification. In the description of the drawings, the same elements are denoted by the same reference numerals, and redundant description will be omitted. In addition, dimensional ratios in the drawings are exaggerated for convenience of description and may be different from actual ratios.

FIG. 7 is a plan view schematically showing a blood glucose meter used for detecting glucose (blood glucose) using the measuring chip according to the present embodiment. In FIG. 7, reference numeral 10 denotes a blood glucose meter; 12 denotes a measuring chip; 14 denotes a measurement part; 18 denotes a chip body; 40 denotes a housing; 42 denotes a control unit; 44 denotes a box body unit; 46 denotes an optical measurement unit; 48 denotes a power button; 50 denotes an operation button; 52 denotes a display; and 54 denotes an ejection lever.

In FIG. 7, a blood glucose meter 10 is configured as a device for measuring glucose (blood glucose) in a blood sample. The blood glucose meter 10 can be mainly used as a personal use operated by a user (subject). The user can also perform his or her blood glucose management by measuring blood glucose before eating. In addition, the blood glucose meter 10 can be used by a medical worker to evaluate the health condition of the subject. In this case, the blood glucose meter 10 may be modified as appropriate so as to be installable in a medical facility or the like.

The blood glucose meter 10 employs the principle of a colorimetric method for optically measuring the content of glucose (blood glucose level) contained in a blood sample. In particular, the blood glucose meter 10 performs blood glucose measurement by a transmission type measurement part 14 that irradiates an analysis sample (blood) with measurement light having a predetermined wavelength and receives light transmitted through the analysis sample.

In the blood glucose meter 10, a measuring chip 12 taking in blood is attached, or blood is taken in the measuring chip 12 in a state where the measuring chip 12 is attached, and glucose is detected by the measurement part 14. The measuring chip 12 may be configured as a disposable type that is discarded every measurement. On the other hand, the blood glucose meter 10 is preferably configured as a portable and robust device so that the user can easily repeat the measurement.

As shown in FIG. 8, the measuring chip 12 includes a chip body 18 formed in a plate shape, and a cavity 20 (liquid cavity) extending in the surface direction of the plate surface inside the chip body 18. In FIG. 8, reference numeral 10 denotes a blood glucose meter; 12 denotes a measuring chip; 14 denotes a measurement part; 16 denotes a device main body; 18 denotes a chip body; 20 denotes a cavity; 20a denotes a distal end opening; 20b denotes a proximal end opening; 22 denotes a long side; 24 denotes a short side; 30 denotes a plate piece; 32 denotes a spacer; 40 denotes a housing; 46 denotes an optical measurement unit; 56 denotes an ejection pin; 56a denotes a rod; 56b denotes a receiving part; 58 denotes an insertion hole; 58a denotes an insertion opening; 59 denotes a measuring hole; 60 denotes a chip attachment part; 60a denotes a flange; 62 denotes a wall portion; 68 denotes a light emitting element; 70 denotes a light emitting part; 72 denotes a light receiving element; 74 denotes a light receiving part; and 76 denotes a coil spring.

As shown in FIG. 8, the chip body 18 is formed in a rectangular shape having a long side 22 long in the insertion and removal direction of the blood glucose meter 10 (the distal and proximal direction of the blood glucose meter 10, that is, the direction B in FIG. 7) and a short side 24 short in the direction A. For example, the length of the long side 22 of the chip body 18 may be set to be twice the length of the short side 24 or more. As a result, a sufficient insertion amount of the measuring chip 12 into the blood glucose meter 10 is ensured.

In addition, the thickness of the chip body 18 is formed to be extremely small (thin) as compared with the side surface formed in a rectangular shape (in FIG. 8, the chip body is illustrated to have a sufficient thickness). For example, the thickness of the chip body 18 is preferably set to ¹⁄₁₀ or less of the short side 24 described above. The thickness of the chip body 18 may be appropriately designed according to the shape of an insertion hole 58 of the blood glucose meter 10.

In the measuring chip 12, the chip body 18 is constituted of a pair of plate pieces 30 and a pair of spacers 32 so as to have the cavity 20.

FIG. 9 is a top view showing the measuring chip of FIG. 7. In FIG. 9, reference numeral 12 denotes a measuring chip; 18 denotes a chip body; 20 denotes a cavity; 20a denotes a distal end opening; 20b denotes a proximal end opening; 22 denotes a long side; 22a denotes an upper long side; 22b denotes a lower long side; 24 denotes a short side; 24a denotes a distal end side; 24b denotes a proximal end side; 26 denotes a reagent; 28 denotes a measuring object; 30 denotes a plate piece; and 32 denotes a spacer. In FIG. 9, the corner portion of the chip body 18 is pointed, but the corner portion may be formed in a round corner, for example. The shape of the chip body 18 is not limited to a thin plate, and may be freely designed. For example, the chip body 18 may be formed in a square shape, another polygonal shape, a circular shape (including an elliptical shape), or the like in a top view.

The cavity 20 provided inside the chip body 18 is located at an intermediate position in the short-axis direction of the chip body 18 and is linearly formed over the longitudinal direction of the chip body 18. The cavity 20 is continuous with a distal end opening 20a formed on a distal end side 24a and a proximal end opening 20b formed on a proximal end side 24b of the chip body 18, and communicates with the outside of the chip body 18. When the cavity 20 takes in blood of the user from the distal end opening 20a, the blood can flow along the extending direction based on the capillary phenomenon. A small amount of blood flows in the cavity 20, and even if the blood moves to the proximal end opening 20b, leakage is suppressed by tension. It should be noted that an absorption part that absorbs blood (for example, a spacer 32 to be described later is made of a porous-body only on the proximal side) may be provided on the proximal end side 24b of the chip body 18.

At a predetermined position of the cavity 20 (for example, a position slightly closer to the proximal end than the midpoint between the distal end opening 20a and the proximal end opening 20b shown in FIG. 9), a reagent (coloring reagent) 26 that reacts with glucose (blood glucose) in blood to change a color corresponding to the glucose (blood glucose) concentration in blood are applied, and a measuring object 28 to be measured by the blood glucose meter 10 is set. The blood flowing in the cavity 20 in the proximal direction comes into contact with a reagent 26 applied to the measuring object 28, and the blood and the reagent 26 react with each other to change a color. In addition, in the longitudinal direction of the cavity 20, the application position of the reagent 26 and the measuring object 28 may be shifted from each other, and for example, the reaction unit to which the reagent 26 is applied may be provided on the upstream side of the measuring object 28 in the blood flow direction.

In the measuring chip 12, the chip body 18 is constituted of a pair of plate pieces 30 and a pair of spacers 32 so as to have the cavity 20. The pair of plate pieces 30 are each formed in the above-described rectangular shape in a side view, and are arranged in the stacking direction. That is, the pair of plate pieces 30 constitute both side surfaces (upper surface and lower surface) of the chip body 18. The plate thickness of each plate piece 30 is very small and may be set to the same dimension of, for example, about 5 to 50 μm. The thicknesses of the two (one set of) plate pieces 30 may be different from each other.

The pair of plate pieces 30 have a strength that maintains the plate shape and is not plastically deformed even when a certain degree of pressing force is applied in a direction orthogonal to the surface direction. Each plate piece 30 is provided with a transparent part or a translucent part so that the measurement light can be transmitted. Further, each plate piece 30 is preferably formed into a flat plate surface having appropriate hydrophilicity so as to allow blood to flow in the cavity 20.

A material constituting each plate piece 30 is not particularly limited, but a thermoplastic resin material, glass, quartz, or the like may be applied. Examples of the thermoplastic resin material include polymer materials such as polyolefin (e.g., polyethylene, polypropylene, etc.), cycloolefin polymer, polyester (e.g., polyethylene terephthalate, polyethylene naphthalate, etc.), polyvinyl chloride, polystyrene, ABS resin, acrylic resin, polyamide, and fluororesin, and mixtures thereof.

Further, the pair of spacers 32 are arranged so as to be sandwiched between the pair of plate pieces 30, and are firmly bonded to the facing surfaces of the plate pieces 30 by a predetermined bonding means (adhesive or the like). That is, each of the spacers 32 is a member that forms the cavity 20 between the pair of plate pieces 30 and the pair of spacers 32 themselves by being disposed between the pair of plate pieces 30 so as to be separated from each other. In this case, one spacer 32 is disposed so as to be in contact with an upper long side 22a of the chip body 18 in FIG. 9 and extend in the distal and proximal direction along the upper long side 22a. The other spacer 32 is disposed so as to be in contact with a lower long side 22b of the chip body 18 in FIG. 9 and extend in the distal and proximal direction along the lower long side 22b.

The material (base material) constituting the pair of spacers 32 is not particularly limited, and examples thereof include various thermoplastic elastomers such as a styrene-based elastomer, a polyolefin-based elastomer, a polyurethane-based elastomer, a polyester-based elastomer, a polyamide-based elastomer, a polybutadiene-based elastomer, a trans-polyisoprene-based elastomer, a fluororubber-based elastomer, and a chlorinated polyethylene-based elastomer. Alternatively, in addition to the thermoplastic elastomer, various elastically deformable materials may be applied, and a structure such as an elastically deformable porous body (for example, sponge) may be applied. Furthermore, the spacer 32 may be applied as a spacer having an adhesive on one or both surfaces of the base material, the adhesive bonding the plate pieces 30 to each other by being in a cured state or a semi-cured state between the pair of plate pieces 30. Furthermore, the spacer 32 may contain the reagent 26 so that the reagent 26 is eluted into the cavity 20.

The plate pieces 30 and the spacers 32 may be hydrophilized. Examples of the method of hydrophilization treatment include a method of applying an aqueous solution containing a hydrophilic polymer such as polyacrylic acid, polyvinylpyrrolidone, or polyacrylamide in addition to a surfactant, polyethylene glycol, polypropylene glycol, hydroxypropylcellulose, and water-soluble silicone, by a dipping method, a spraying method, or the like and a method of plasma irradiation, glow discharge, corona discharge, ultraviolet irradiation (for example, excimer light irradiation), and these methods may be used alone or in combination.

Next, the device main body 16 of the blood glucose meter 10 will be described. As shown in FIG. 7, the blood glucose meter 10 has a housing 40 constituting an external appearance. The housing 40 includes a box body unit 44 having a size that is easily gripped and operated by the user and accommodating a control unit 42 of the blood glucose meter 10 therein, and a cylindrical optical measurement unit 46 protruding from one side (distal end side) of the box body unit 44 in the distal direction and accommodating the measurement part 14 of the optical system therein. A power button 48, an operation button 50, and a display 52 are provided on the upper surface of the box body unit 44, and an ejection lever 54 is provided on the upper surface of the optical measurement unit 46.

The power button 48 is operated by the user to switch between activation and deactivation of the blood glucose meter 10. In the activated blood glucose meter 10, the operation button 50 functions as an operation unit for measuring and displaying a blood glucose level, switching display of a measurement result (including a past measurement result), and the like based on a user's operation. The display 52 is constituted by a liquid crystal, an organic EL, or the like, and displays information to be provided to a user in a measurement operation, such as a measurement result display, an error display, or the like.

The ejection lever 54 is provided so as to be movable in the distal and proximal direction, and releases a lock of an ejection pin (not shown) provided in the optical measurement unit 46 so that the ejection pin can advance in the distal direction.

On the other hand, the optical measurement unit 46 of the device main body 16 extends long in the distal direction from the box body unit 44 in order to press the distal end against the user's finger or the like. As shown in FIG. 8, the optical measurement unit 46 is provided with a chip attachment part 60 having an insertion hole 58 and a measurement part 14 for optically detecting glucose (blood glucose) in blood.

The chip attachment part 60 is made of a material having high hardness (rigidity) (for example, stainless steel), and is formed in a cylindrical shape having a flange 60a protruding outward on the distal end side and having a predetermined length in the axial direction. The chip attachment part 60 is positioned and fixed over the distal end surface and the axial center portion (central portion) of the optical measurement unit 46 made of a resin material. As shown in FIG. 10A, a fixed wall 46a for firmly fixing the chip attachment part 60 is formed to protrude from the inner surface of the optical measurement unit 46. In FIG. 10A, reference numeral 12 denotes a measuring chip; 14 denotes a measurement part; 16 denotes a device main body; 20 denotes a cavity; 26 denotes a reagent; 28 denotes a measuring object; 30 denotes a plate piece; 32 denotes a spacer; 40 denotes a housing; 46 denotes an optical measurement unit; 46a denotes a fixed wall; 56 denotes an ejection pin; 56a denotes a rod; 56b denotes a receiving part; 58 denotes an insertion hole; 58a denotes an insertion opening; 59 denotes a measuring hole; 60 denotes a chip attachment part; 60a denotes a flange; 62 denotes a wall portion; 64 denotes an element accommodating space; 66 denotes a light guide portion; 68 denotes a light emitting element; 68a denotes a first light emitting element; 68b denotes a second light emitting element; 70 denotes a light emitting part; 72 denotes a light receiving element; 74 denotes a light receiving part; and 76 denotes a coil spring.

Examples of the material constituting the chip attachment part 60 include metals such as stainless steel and titanium, aluminum subjected to alumite film treatment, liquid crystal polymers, plastics to which fillers such as glass and mica are added, plastics whose surfaces are hard-coated with nickel plating or the like, carbon fibers, fine ceramics, and the like, which are hard, whose dimensions do not easily change, are not easily worn even when the measuring chip is repeatedly inserted and removed, and can be processed with high dimensional accuracy. In particular, if a metal material is used, the insertion hole 58 can be easily formed with high dimensional accuracy when the chip attachment part 60 is manufactured (by injection molding, press molding, or the like). In the device main body 16, the optical measurement unit 46 itself may be formed of a hard material (for example, a metal material) to integrally mold the chip attachment part 60.

The insertion hole 58 is provided in the axial center portion of the chip attachment part 60 by being surrounded by the wall portion 62 of the chip attachment part 60. The insertion hole 58 is formed in a rectangular cross-sectional shape that is long in the insertion direction (direction B) and short in the left-right width direction (direction A). The insertion hole 58 has a predetermined depth from the distal end surface toward the back portion (proximal direction) in a state where the chip attachment part 60 is fixed to the optical measurement unit 46.

An insertion opening 58a, which is continuous with the insertion hole 58 and communicates with the outside, is formed on the distal end side of the chip attachment part 60. The dimension of the insertion opening 58a in the insertion direction (direction B) coincides with the dimension of the short side 24 of the measuring chip 12 (length in the direction A). In addition, as shown in FIG. 10A, the dimension of the insertion opening 58a in the left-right width direction, that is, the distance between the pair of wall portions 62 constituting the side surfaces of the insertion hole 58 is substantially the same as the thickness of the measuring chip 12 in the stacking direction (Tall in FIG. 10A).

The chip attachment part 60 forms a pair of element accommodating spaces 64 and in cooperation with the fixed wall 46a of the optical measurement unit 46 at a midway position where the insertion hole 58 (measuring hole 59) extends. The pair of element accommodating spaces 64 are a part of the measurement part 14, are provided at positions facing each other with the insertion hole 58 interposed therebetween, and communicate with the measuring hole 59 via each light guide portion 66 formed by the chip attachment part 60.

In the measurement part 14, a light emitting part 70 is configured by accommodating a light emitting element 68 in one element accommodating space 64, and a light receiving part 74 is configured by accommodating a light receiving element 72 in the other element accommodating space 64. The light guide portion 66 of the chip attachment part 60 is formed as a circular hole having an appropriate diameter, thereby serving as a so-called aperture.

The light emitting element 68 of the light emitting part 70 include a first light emitting element 68a that irradiates the measuring chip 12 with measurement light having a first wavelength and a second light emitting element 68b that irradiates the measuring chip 12 with measurement light having a second wavelength different from the first wavelength (not shown in FIG. 8). The first light emitting element 68a and the second light emitting element 68b are arranged side by side at a position facing the light guide portion 66 of the element accommodating space 64.

The light emitting element 68 (the first and second light emitting elements 68a and 68b) may be formed of a light emitting diode (LED). The first wavelength is a wavelength for detecting the changing color density of the reagents 26 according to the blood glucose level, and is, for example, 600 nm to 680 nm. The second wavelength is a wavelength for detecting the erythrocyte concentration in blood, and is, for example, 510 nm to 540 nm. The control unit 42 in the box body unit 44 supplies a driving current to make the first and second light emitting elements 68a and 68b emit light at predetermined timings. In this case, the blood glucose level obtained from the changing color density is corrected using the hematocrit value obtained from the erythrocyte concentration to obtain the blood glucose level. Note that noise caused by blood cells may be corrected by measuring at another measurement wavelength.

The light receiving part 74 is configured by arranging one light receiving element 72 at a position facing the light guide portion 66 of the element accommodating space 64. The light receiving part 74 receives the transmitted light from the measuring chip 12, and may be formed of, for example, a photodiode (PD).

An ejection pin 56 (eject portion) connected to the ejection lever 54 is provided at the bottom (proximal end surface) of the insertion hole 58. The ejection pin 56 is provided with a rod 56a extending along the axial direction of the optical measurement unit 46 and a receiving part 56b having a large diameter on the outside in the radial direction at the distal end portion of the rod 56a. The proximal end side 24b of the measuring chip 12 inserted into the insertion hole 58 contacts the receiving part 56b. A coil spring 76 surrounding the ejection pin 56 in a non-contact manner is provided between the bottom of the insertion hole 58 and the receiving part 56b of the ejection pin 56. The coil spring 76 elastically supports the receiving part 56b of the ejection pin 56.

When the insertion of the measuring chip 12 is completed, as shown in FIG. 10B, the measuring object 28 of the measuring chip 12 is disposed at a position overlapping the light guide portion 66. In FIG. 10B, reference numeral 12 denotes a measuring chip; 14 denotes a measurement part; 16 denotes a device main body; 20 denotes a cavity; 20a denotes a distal end opening; 26 denotes a reagent; 30 denotes a plate piece; 32 denotes a spacer; 40 denotes a housing; 46 denotes an optical measurement unit; 46a denotes a fixed hole; 56 denotes an ejection pin; 56a denotes a rod; 56b denotes a receiving part; 60 denotes a chip attachment part; 60a denotes a flange; 62 denotes a wall portion; 68 denotes a light emitting element; 68a denote a first light emitting element; 68b denotes a second light emitting element; 70 denotes a light emitting part; 72 denotes a light receiving element; 74 denotes a light receiving part; and 76 denotes a coil spring.

The ejection pin 56 is displaced in the proximal direction when the receiving part 56b is pressed in accordance with the insertion of the measuring chip 12 by the user, and is locked (fixed) by a lock mechanism (not shown) provided in the housing 40. The coil spring 76 elastically contracts according to the displacement of the receiving part 56b. When the ejection pin 56 is slightly moved by the operation of the ejection lever 54 by the user, the lock of the lock mechanism is released, and the coil spring 76 slides in the distal direction by the elastic restoring force. As a result, the measuring chip 12 is pushed out by the ejection pin 56 and taken out from the insertion hole 58.

Referring back to FIG. 7, the control unit 42 of the device main body 16 includes, for example, a control circuit having an arithmetic unit, a storage unit, and an input/output unit (not shown). A well-known computer can be applied to the control unit 42. For example, under the operation of the operation button 50 by the user, the control unit 42 drives and controls the measurement part 14 to detect and calculate glucose in blood, and displays the calculated blood glucose level on the display 52.

For example, in the blood glucose meter 10 that measures an analyte (for example, glucose) by transmitting measurement light to the measuring chip 12, the control unit 42 calculates a measurement result based on the Beer-Lambert law represented by the following formula (D).

[Math. 4]

$$\log_{10}(l_1/l_0) = -\alpha L \quad \text{Formula (D):}$$

In the above formula (D), $l_0$ is the intensity of light before entering the blood sample, $l_1$ is the intensity of light after exiting the blood sample, $\alpha$ is the absorption coefficient, and L is the distance (cell length) through which the measurement light passes.

EXAMPLES

The effects of the present invention will be described with reference to the following Examples and Comparative Examples. However, the technical scope of the present invention is not limited to the following examples. In the following Examples, unless otherwise specified, the operation was carried out at room temperature (25° C.). Unless otherwise specified, "%" and "parts" mean "% by mass" and "parts by mass", respectively.

Preparation Example 1: Synthesis of Tetrazolium Compound 1

The compound (2-(6-methoxybenzothiazolyl)-3-(3-sulfo-4-methoxy-phenyl)-5-(2,4-disulfophenyl)-2H-tetrazolium salt:tetrazolium compound 1) having the following structure (MW=693) was synthesized according to the following procedure.

[Chem. 22]

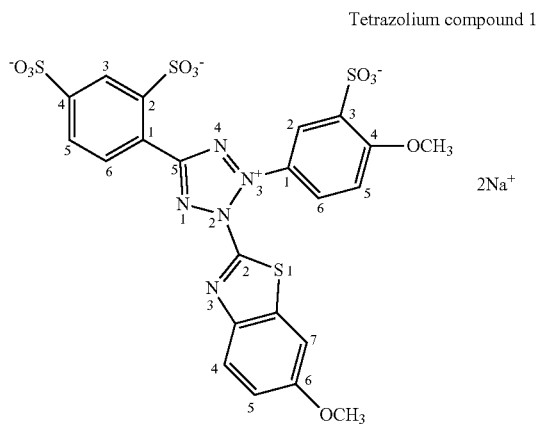

Tetrazolium compound 1

1. Synthesis of Hydrazone Compound 1

1.59 g pf disodium 4-formylbenzene-1,3-disulfonate (manufactured by Tokyo Chemical Industry Co., Ltd.) and 1.0 g of 2-hydrazino-6-methoxy-1,3-benzothiazole (manufactured by Santa Cruz Biotechnology) were suspended in 60 mL of RO water. This suspension was heated and stirred in a water bath at 60° C. for 2 hours under acetic acid acidity. After completion of the heating and stirring, the solvent was removed. The residue was washed with isopropanol and the precipitate was filtered off. The precipitate was dried in a draft to obtain hydrazone compound 1. 1.8 g was recovered, and the yield was 70% by mass.

2. Synthesis of Formazan Compound 1

0.76 g of the hydrazone compound 1 obtained in 1. above was dissolved in a mixture of 10 mL of RO water and 10 mL of N,N-dimethylformamide (DMF) to prepare a hydrazone compound 1 solution. 0.264 g of p-anisidine-3-sulfonic acid (manufactured by Tokyo Chemical Industry Co., Ltd.) was suspended in 4.09 mL of RO water, and 130 µL of 10N NaOH was added to dissolve the p-anisidine-3-sulfonic acid. While the mixture was kept at 0° C., 280 µL of 9.6N HCl was added, and sodium nitrite solution was added dropwise to perform diazotization. The diazotized solution was kept at −20° C. and added dropwise to the hydrazone compound 1 solution. After completion of the dropwise addition, 300 µL of 10N NaOH was added dropwise, and the mixture was stirred at room temperature (25° C.) for 2 hours to prepare a solution containing formazan compound 1 (formazan compound 1 solution). The formazan compound 1 solution was neutralized with 9.6N HCl and the solvent was removed. The resulting residue was washed with isopropanol, and the precipitate was filtered off. The precipitate was dried to obtain formazan compound 1.

3. Purification of Formazan Compound 1 and Synthesis of Tetrazolium Compound 1

The formazan compound 1 obtained in 2. above was dissolved in 10 mL of RO water to prepare a formazan compound 1 solution. A disposable column (size: 20 cm×5 cm) was filled with a filler for column chromatography (COSMOSIL 40$C_{18}$-PREP, manufactured by Nacalai Tesque, Inc.), and the column was set in a column fractionation system (manufactured by Nihon Buchi Co., Ltd., trade name: Sepacore). This column system was used to purify the formazan compound 1 solution. The solvent of the collected fractions was removed, and 15 mL of methanol, 250 µL of 9.6N HCl, and 5 mL of 15% ethyl nitrite ($CH_3CH_2NO_2$)-ethanol solution were added to the obtained solid components, followed by stirring for 72 hours at room temperature (25° C.) in the dark.

4. Recovery of Tetrazolium Compound 1

Diethyl ether was added to the reaction solution obtained in 3. above to precipitate the tetrazolium compound 1. The precipitate was centrifuged, and the supernatant was removed, followed by washing with diethyl ether. The obtained precipitate was dried in a draft to obtain tetrazolium compound 1 (120 mg, yield: 11.8% by mass). The maximum absorption wavelength ($\lambda$max) of the tetrazolium compound 1 thus obtained was measured and found to be 630 nm.

Examples 1 to 6 and Comparative Example 1:
Evaluation with Blood Glucose Meter Sensor <Preparation of Coating Liquid>

First, an aqueous solution (pH 6.5 to 7) containing glucose dehydrogenase (GDH-FAD) ("GDH" in the table) as an oxidoreductase, disodium 1,3-benzenedisulfonate (DSB, manufactured by Alfa Aear) as a light-scattering adjustment reagent, tetrazolium compound 1 synthesized in Preparation Example 1 as a chromogenic indicator, nickel acetate ("Ni acetate" in the table) as a transition metal compound, and sodium hydroxide aqueous solution (appropriate amount) as a pH adjustor was prepared so as to have the composition shown in Table 1 below, and coating liquids 1 to 6 (Examples 1 to 6) and comparative coating liquid 1 (Comparative Example 1) were obtained.

<Preparation of Blood Glucose Level Measuring Chip>

1. Preparation of Reagent Strip

Each of Coating Liquids 1 to 6 and Comparative Coating Liquid 1 prepared in the above <Preparation of Coating Liquid> was applied onto a polyethylene terephthalate (PET) film (manufactured by Toray Industries, Inc., trade name: Lumirror T60, thickness: 188 µm, 8 mm×80 mm) placed on a stage using an inkjet apparatus (manufactured by Microjet Co., Ltd., Labojet-500Bio) with a patterning accuracy within ±5 µm and a head discharge amount of 1 µL to 1000 µL, and dried overnight at room temperature (25° C.). After drying, the PET film on which the reagent layer was formed was cut into a predetermined size to prepare a reagent strip.

2. Measurement of Amount of Each Component Applied

The amount (concentration) of each component applied to each reagent strip prepared in 1. above was determined as follows. Specifically, in a state of being assembled into a blood glucose meter sensor (chip shape) described later, 1000 µL of RO water was added into the chip to completely dissolve the blood glucose level measuring reagent, thereby preparing a sample. The concentration of the coloring reagent in the sample was determined by UPLC (ultra performance liquid chromatograph SHIMADZU NEXERA X2, manufactured by Shimadzu Corporation). From the mass (mg) of the coloring reagent applied to each chip, the concentration of the coloring reagent (tetrazolium compound 1) when RO water flows into the reagent part space and dissolves was calculated, and the results are shown in Table 2 below. Further, from the concentration ratio of the coating liquid described in Table 1 above, the concentration of the reagent component when RO water flows into the reagent part space and fills the reagent part space volume (that is, when dissolved) was calculated for the components other than the chromogenic indicator, and the results are shown in Table 2 below. The mass of each component per one blood glucose level measuring chip can be calculated from the reagent part space volume and the concentration shown in Table 2 below.

TABLE 1

Preparation of Blood Glucose Level Measuring Reagent

| Coating liquid | Example 1 | Example 2 | Example 3 | Example 4 | Example 5 | Example 6 | Comparative Example 1 |
|---|---|---|---|---|---|---|---|
| GDH (MU/L) | 2.10 | 4.20 | 7.40 | 8.39 | 7.40 | 7.40 | 10.41 |
| Tetrazolium compound 1 (mM) | 8.02 | 16.03 | 28.25 | 32.06 | 28.25 | 28.25 | 103.24 |
| Ni acetate (mM) | 40.08 | 80.15 | 141.25 | 153.19 | 134.98 | 134.98 | 383.45 |
| DSB (mM) | 2.40 | 4.81 | 8.48 | 17.95 | 32.21 | 48.03 | 117.99 |

TABLE 2

Each Component Amount of Blood Glucose Level Measuring Reagent (RO water)

| | Example 1 | Example 2 | Example 3 | Example 4 | Example 5 | Example 6 | Comparative Example 1 |
|---|---|---|---|---|---|---|---|
| GDH (MU/L) | 3.28 | 6.55 | 13.10 | 13.09 | 13.10 | 13.10 | 16.24 |
| Tetrazolium compound 1 (mM) | 12.5 | 25 | 50 | 50 | 50 | 50 | 161 |
| Ni acetate (mM) | 62.5 | 125 | 250 | 238.9 | 238.9 | 238.9 | 598 |
| DSB (mM) | 3.75 | 7.5 | 15 | 28 | 57 | 85 | 184 |
| Ni acetate + DSB (mM) | 66.25 | 132.5 | 265 | 266.9 | 295.9 | 323.9 | 782 |
| (DSB/Ni acetate) molar ratio | 0.06 | 0.06 | 0.06 | 0.12 | 0.24 | 0.36 | 0.30 |
| (Ni acetate/Tetrazolium compound 1) molar ratio | 5.0 | 5.0 | 5.0 | 4.8 | 4.8 | 4.8 | 3.7 |

3. Assembly of Blood Glucose Meter Sensor (Blood Glucose Measuring Chip)

FIG. 11A is a pattern diagram showing the assembly of the blood glucose meter sensor (blood glucose measuring chip). In FIG. 11A, reference numeral 2 denotes a reagent strip; 3 denotes a reagent application surface; 4 denotes a double-sided tape; 5 denotes a PET film; 6 denotes a flow path; and 7 denotes a PET film. In FIG. 11A, a chip base was prepared in which a double-sided tape 4 (manufactured by Nitto Denko Corporation, trade name: double-sided adhesive tape, thickness: 50 μm) was formed as a spacer and an adhesive portion on both sides of a PET film 5 (manufactured by 3M Corporation, trade name: hydrophilic-treated polyester film 9901P, thickness: 100 μm) as a second base material. The reagent strip 2 prepared in 1. above was attached to the chip base such that the reagent layer 3 (reagent application surface) faced the PET film 5 serving as the chip base and was positioned at the center of the flow path 6.

In FIG. 11A, the reagent strip 2 is placed on a pair of double-sided tapes 4 as spacers arranged at both ends of the PET film 5 with the reagent application surface 3 facing downward. Next, a PET film having the same shape as the PET film 5 is prepared. A double-sided tape (manufactured by 3M Co., Ltd., trade name: double-sided adhesive tape, thickness: 80 μm) (not shown) is attached to both sides in the longitudinal direction of the surface of the PET film that faces the reagent strip 2 to form a PET film 7. The PET film 7 was attached onto the spacer and the double-sided tape 4 (adhesive portion) from above the reagent strip 2, thereby obtaining the blood glucose level measuring chips 1 to 6 (Examples 1 to 6, respectively) and the comparative blood glucose level measuring chip 1 (Comparative Example 1) having the blood flow path 6 on the inner surface in a stepped shape. FIG. 11B is a longitudinal or transverse cross-sectional view of a blood glucose meter sensor (measuring chip). In FIG. 11B, reference numeral 1 denotes a measuring chip; 2 denotes a reagent strip; 3 denotes a reagent application surface; 4 denotes a double-sided tape; 5 denotes a PET film; and 7 denotes a PET film. As shown in FIG. 11B, for the flow path length (L1), flow path width (W), and flow path thickness (t1) of the flow path part (flow path 6), and the flow path length (L2), flow path width (W), and flow path thickness (t2) of the reagent part (measurement part) 3 corresponding to the reagent application portion, the sizes shown in Table 3 below were used. In FIG. 11B, the flow path of the blood glucose meter sensor (measuring chip) includes a reagent part in which a reagent application surface is arranged and a flow path part in which no reagent application surface is arranged in the flow path.

TABLE 3

| Flow path part | | Reagent part (measurement part) | |
|---|---|---|---|
| Length L1 | 9 mm | Length L2 | 3 mm |
| Width W | 1.5 mm | Width W | 1.5 mm |
| Thickness t1 | 0.13 mm | Thickness t2 | 0.05 mm |

Here, the volume of the measurement part is a volume B of a gap (i.e., a region in which the blood glucose level measuring reagent and blood are in a dissolved state) sandwiched between a reagent formation surface, which is a surface in the flow path on which the reagent layer 3 made of the blood glucose level measuring reagent is formed, and a facing surface facing the reagent layer 3 in the thickness direction of the reagent layer 3, among the inner walls defining the flow path 6. That is, the volume B is a space calculated by L2×W×t2 in FIG. 11B.

The length L1 of the flow path part in the direction orthogonal to the chip thickness direction (flow path longitudinal direction) is not particularly limited and may be appropriately selected depending on the purpose, but is preferably 5 to 10 mm. Here, if the length L1 is long, it is advantageous in that it is easy to attach (insert) to the component measuring device and that the entry of disturbance light into the optical measurement unit is reduced. When the length L1 is short, it is advantageous in that the amount of the specimen can be reduced. Therefore, the upper limit and the lower limit of the length L1 are determined in consideration of the ease of attachment (insertion) to the component measuring device, the influence of disturbance light, and the balance of the amount of the specimen. The length L2 of the reagent part in the direction orthogonal to the chip thickness direction (flow path longitudinal direction) is not particularly limited and may be appropriately selected depending on the purpose, but is preferably 1 to 4 mm. Here, the longer the length L2, the larger the area of the irradiation spot in the longitudinal direction, which is advantageous in that the measurement can be performed with high accuracy, but the shorter the length L2, the smaller the amount of the specimen, which is advantageous. Therefore, the upper limit and the lower limit of the distance L2 are determined in consideration of the balance between the measurement accuracy and the amount of the specimen.

To the inlet of the flow path of each of the produced blood glucose meter sensors, 4 μL of each of human whole blood sample 1 (Ht20, BG0) (hematocrit value: 20%, glucose concentration: 0 mg/dL), whole blood sample 2 (Ht20, BG400) (hematocrit value: 20%, glucose concentration: 400 mg/dL), whole blood sample 3 (Ht40, BG0) (hematocrit value: 40%, glucose concentration: 0 mg/dL), whole blood sample 4 (Ht40, BG400) (hematocrit value: 40%, glucose concentration: 400 mg/dL), whole blood sample 5 (Ht60, BG0) (hematocrit value: 60%, glucose concentration: 0 mg/dL), and whole blood sample 6 (Ht60, BG400) (hematocrit value: 60%, glucose concentration: 400 mg/dL) was applied. The amount of each component of the blood glucose level measuring reagent shown in Table 2 above is the concentration in the space of the volume B when a sample having a hematocrit value of 0 (aqueous solution having a glucose concentration of 0 mg, i.e., RO water) is introduced into the blood glucose meter sensor. As described above, the amount of each component needs to be converted into a numerical value in plasma in consideration of the hematocrit value of the blood sample. For example, because the nickel acetate of Example 1 is 62.5 mM in a sample having a hematocrit value of 0, in the whole blood sample having a hematocrit value of 40, the nickel acetate of Example 1 is about 104.17 (=62.5×1/0.6) mM. The amount of each component of the reagent after conversion in each of the whole blood samples is shown in Tables 4 to 6 below (hematocrit values of 20 (Ht20), 40 (Ht40), and 60 (Ht60), respectively).

TABLE 4

Each Component Amount of Blood Glucose Level Measuring Reagent (Ht20)

| | Example 1 | Example 2 | Example 3 | Example 4 | Example 5 | Example 6 | Comparative Example 1 |
|---|---|---|---|---|---|---|---|
| GDH (MU/L) | 4.10 | 8.19 | 16.37 | 16.36 | 16.37 | 16.37 | 20.30 |
| Tetrazolium compound 1 (mM) | 15.63 | 31.25 | 62.50 | 62.50 | 62.50 | 62.50 | 201.25 |
| Ni acetate (mM) | 78.13 | 156.25 | 312.50 | 298.63 | 298.63 | 298.63 | 747.50 |
| DSB (mM) | 4.69 | 9.38 | 18.75 | 35.00 | 71.25 | 106.25 | 230.00 |
| Ni acetate + DSB (mM) | 82.8 | 165.6 | 331.3 | 333.6 | 369.9 | 404.9 | 977.5 |
| (DSB/Ni acetate) molar ratio | 0.06 | 0.06 | 0.06 | 0.12 | 0.24 | 0.36 | 0.31 |
| (Ni acetate/Tetrazolium compound 1) molar ratio | 5.0 | 5.0 | 5.0 | 4.78 | 4.78 | 4.78 | 3.7 |

TABLE 5

Each Component Amount of Blood Glucose Level Measuring Reagent (Ht40)

| | Example 1 | Example 2 | Example 3 | Example 4 | Example 5 | Example 6 | Comparative Example 1 |
|---|---|---|---|---|---|---|---|
| GDH (MU/L) | 5.46 | 10.92 | 21.83 | 21.81 | 21.83 | 21.83 | 27.066 |
| Tetrazolium compound 1 (mM) | 20.83 | 41.67 | 83.33 | 83.33 | 83.33 | 83.33 | 268.33 |
| Ni acetate (mM) | 104.17 | 208.33 | 416.67 | 398.17 | 398.17 | 398.17 | 996.67 |
| DSB (mM) | 6.25 | 12.50 | 25.00 | 46.67 | 95.00 | 141.67 | 306.67 |
| Ni acetate + DSB (mM) | 110.4 | 220.8 | 441.7 | 444.8 | 493.2 | 539.8 | 1303.3 |
| (DSB/Ni acetate) molar ratio | 0.06 | 0.06 | 0.06 | 0.12 | 0.24 | 0.36 | 0.31 |
| (Ni acetate/Tetrazolium compound 1) molar ratio | 5.0 | 5.0 | 5.0 | 4.78 | 4.78 | 4.78 | 3.7 |

TABLE 6

Each Component Amount of Blood Glucose Level Measuring Reagent (Ht60)

| | Example 1 | Example 2 | Example 3 | Example 4 | Example 5 | Example 6 | Comparative Example 1 |
|---|---|---|---|---|---|---|---|
| GDH (MU/L) | 8.19 | 16.38 | 32.74 | 32.72 | 32.74 | 32.74 | 40.60 |
| Tetrazolium compound 1 (mM) | 31.25 | 62.50 | 125.00 | 125.00 | 125.00 | 125.00 | 402.50 |
| Ni acetate (mM) | 156.25 | 312.50 | 625.00 | 597.25 | 597.25 | 597.25 | 1495.00 |
| DSB (mM) | 9.38 | 18.75 | 37.50 | 70.00 | 142.50 | 212.50 | 460.00 |

TABLE 6-continued

Each Component Amount of Blood Glucose Level Measuring Reagent (Ht60)

|  | Example 1 | Example 2 | Example 3 | Example 4 | Example 5 | Example 6 | Comparative Example 1 |
|---|---|---|---|---|---|---|---|
| Ni acetate + DSB (mM) | 165.6 | 331.3 | 662.5 | 667.3 | 739.8 | 809.8 | 1955.0 |
| (DSB/Ni acetate) molar ratio | 0.06 | 0.06 | 0.06 | 0.12 | 0.24 | 0.36 | 0.31 |
| (Ni acetate/Tetrazolium compound 1) molar ratio | 5.0 | 5.0 | 5.0 | 4.78 | 4.78 | 4.78 | 3.7 |

Each whole blood sample was prepared as follows. First, whole blood was collected in a blood collection tube containing heparin, the hematocrit value of the whole blood sample was measured, and plasma obtained by separation in advance was added as appropriate, or the plasma of the whole blood sample was withdrawn to prepare a whole blood sample such that the hematocrit value of the whole blood sample became a predetermined value (Ht20, Ht40, and Ht60). Next, a high-concentration glucose solution (40 g/dL) was appropriately added to the hematocrit value-adjusted whole blood sample to prepare whole blood samples having a blood glucose concentration of 400 mg/dL (Ht20, Ht40, and Ht60, 400 mg/dL). In addition, whole blood samples (Ht20, Ht40, and Ht60) having a blood glucose concentration of 100 mg/dL were prepared in the same manner as described above. Glucose oxidase (GLO-201, manufactured by Toyobo Co., Ltd.) (0.1 mg) was added to each of the whole blood samples (Ht20, Ht40, and Ht60, 100 mg/dL) 1 mL having the respective hematocrit values. After the addition, the mixture was allowed to stand at room temperature (25° C.) for 5 minutes to prepare whole blood samples having a blood glucose concentration of 0 mg/dL (Ht20, Ht40, and Ht60, 0 mg/dL).

Each of the whole blood samples 1 to 6 was applied to the reagent part of the chip prepared above, and after 9 seconds, the spectrum in the wavelength range of 400 to 1000 nm was measured using a fiber spectrophotometer according to the methods described in the above <Spectrum analysis>.

Based on these spectra, the average transmittance difference was calculated and the results are shown in Table 7. Here, the "average transmittance difference" is a difference ($=aveT_{analyte}(\%)-aveT_{Sample}(\%)$) between the average transmittance ($aveT_{analyte}(\%)$) of the analysis sample (after mixing the reagent) in the wavelength region 850 to 1000 nm and the average transmittance ($aveT_{Sample}(\%)$) of the whole blood sample (before mixing the reagent) in the wavelength region 850 to 1000 nm.

In addition, the transmittance difference (absolute value) for the whole blood samples 3 and 4 was calculated, and the results are shown in Table 8. Here, the "transmittance difference (absolute value)" is the maximum value among the absolute values of the difference ($=T_{analyte}(\%)-T_{Sample}(\%)$) between the transmittance ($T_{analyte}(\%)$) of the analysis sample (after mixing the reagent) in the wavelength region 850 to 1000 nm and the transmittance ($T_{Sample}(\%)$) of the whole blood sample (before mixing the reagent) in the wavelength region 850 to 1000 nm.

TABLE 7

| | Average transmittance difference (%) | | | | | | |
|---|---|---|---|---|---|---|---|
| Whole blood sample | Example 1 | Example 2 | Example 3 | Example 4 | Example 5 | Example 6 | Comparative Example 1 |
| 1 (Ht20, BG0) | −4.2 | −8.6 | −4.1 | | | | 23.6 |
| 2 (Ht20, BG400) | −3.9 | −7.5 | −2.4 | | | | 21.9 |
| 3 (Ht40, BG0) | −4.4 | −5.2 | −3.8 | 8.6 | 7.0 | 8.7 | 23.2 |
| 4 (Ht40, BG400) | −3.7 | −3.8 | −3.6 | 7.7 | 7.4 | 8.2 | 20.0 |
| 5 (Ht60, BG0) | −4.8 | −7.4 | −7.8 | | | | 18.5 |
| 6 (Ht60, BG400) | −4.6 | −6.6 | −6.5 | | | | 15.4 |

TABLE 8

| | Transmittance difference (absolute value) (%) | | | | | | |
|---|---|---|---|---|---|---|---|
| Whole blood sample | Example 1 | Example 2 | Example3 | Example 4 | Example 5 | Example 6 | Comparative Example 1 |
| 3 (Ht40, BG0) | 5.35 | 6.02 | 4.28 | 9.3 | 7.6 | 9.5 | 28.7 |
| 4 (Ht40, BG400) | 4.50 | 4.44 | 4.16 | 8.3 | 8.1 | 8.9 | 26.7 |

In addition, spectra of the whole blood samples (Ht20) 1 and 2 using the reagent of Example 1 are shown in FIG. 1, spectra of the whole blood samples (Ht40) 3 and 4 using the reagent of Example 1 are shown in FIG. 2, spectra of the whole blood samples (Ht60) 5 and 6 using the reagent of Example 1 are shown in FIG. 3, spectra of the whole blood samples (Ht20) 1 and 2 using the reagent of Comparative Example 1 are shown in FIG. 4, spectra of the whole blood samples (Ht40) 3 and 4 using the reagent of Comparative Example 1 are shown in FIG. 5, and spectra of the whole blood samples (Ht60) 5 and 6 using the reagent of Comparative Example 1 are shown in FIG. 6, respectively. In the figures, "T %" represents "transmittance (%)".

From these results, by using the reagents of Examples 1 to 6, the difference in average transmittance between the inside and outside of erythrocytes can be significantly reduced as compared with the case of using the reagent of Comparative Example 1. That is, the scattered light generated in the analysis sample after mixing the reagent and the scattered light generated in the specimen can be made close to each other. Therefore, it is considered that by using the reagents of Examples 1 to 6, the analyte concentration in the specimen can be measured with high accuracy by reducing the influence of the baseline fluctuation derived from the scattered light. The present method can further improve the accuracy even when a correction based on blood information such as a hematocrit value or a hemoglobin amount is applied. In addition, the results in Table 8 show that when the reagents of the present invention are used, the difference in transmittance is within 10% over the entire wavelength region of 850 to 1000 nm (that is, the scattered light before and after mixing the reagent is substantially the same over the entire wavelength range).

Examples 7 to 12 and Comparative Example 2: Evaluation of Solubility

The solubility in whole blood samples having a hematocrit value of 60% was evaluated as follows. In the same manner as in Examples 1 to 6 and Comparative Example 1, blood glucose level measuring chips 7 to 12 (Examples 7 to 12, respectively) and a comparative blood glucose level measuring chip 2 (Comparative Example 2) were produced.

2 µL of plasma was applied to the flow path inlet of each of the produced blood glucose level measuring chips. When an actual whole blood sample is used, it is substantially difficult to find the solubility due to the presence of erythrocytes. Therefore, the solubility was evaluated on the assumption that plasma (2 µL) contained in 5 µL of a whole blood sample having a hematocrit value of 60% was applied. The dissolved state of the reagent 9 seconds after the applying of the plasma was visually observed. The results are shown in Table 9 below. In the table, ○ indicates that the reagent was completely dissolved, and x indicates that the reagent remained undissolved.

This application is based on Japanese Patent Application No. 2018-040887, filed on Mar. 7, 2018, the disclosure of which is incorporated by reference in its entirety.

REFERENCE SIGNS LIST

1 Blood glucose meter sensor (measuring chip)
2 Reagent strip
3 Reagent application surface
4 Double-sided tape
5 PET film
6 Flow path
7 PET film
10 Blood glucose meter
12 Measuring chip
14 measurement part
16 Device main body
18 Chip body
20 Cavity
20*a* Distal end opening
20*b* Proximal end opening
22 Long side
22*a* Upper long side
22*b* Lower long side
24 Short side
24*a* Distal end side
24*b* Proximal end side
26 Reagent
28 Measuring object
30 Plate piece
32 Spacer
40 Housing
42 Control unit
44 Box body unit
46 Optical measurement unit
48 Power button
50 Operation button
52 Display
54 Ejection lever
56 Ejection pin
56*a* Rod
56*b* Receiving part
58 Insertion hole
58*a* Insertion opening
59 Measuring hole
60 Chip attachment part
60*a* Flange
62 Wall portion
64 Element accommodating space
66 Light guide portion
68 Light emitting element
70 Light emitting part
72 Light receiving element
74 Light receiving part
76 Coil spring

TABLE 9

| | Example 7 | Example 8 | Example 9 | Example 10 | Example 11 | Example 12 | Comparative Example 2 |
|---|---|---|---|---|---|---|---|
| Dissolved state of reagent | ○ | ○ | ○ | ○ | ○ | ○ | x |

The invention claimed is:

1. A method for measuring an analyte concentration in a specimen, comprising:
    (1) providing the specimen;
    (2) mixing the specimen with a coloring reagent, an oxidoreductase, and a light-scattering adjustment reagent, and a transition metal compound to obtain an analysis sample having substantially the same scattered light as the specimen, wherein a mixing ratio of the light-scattering adjustment reagent to a transition metal compound (defined as mol of the light-scattering adjustment reagent to 1 mol of the transition metal compound) is more than 0 mol and is 0.24 mol or less; and
    (3) measuring the analyte concentration by using the analysis sample.

2. The method according to claim 1, wherein the coloring reagent is 2-substituted benzothiazolyl-3-substituted phenyl-5-substituted sulfonated phenyl-2H-tetrazolium salt represented by the following formula (2):

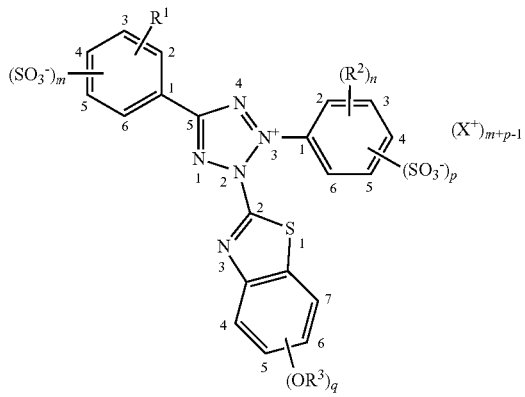

(2)

wherein $R^1$ is any one selected from the group consisting of a hydrogen atom, a hydroxy group, a methoxy group, and an ethoxy group; $R^2$ is any one selected from the group consisting of a nitro group, —$OR^4$, and a carboxyl group; $R^3$ is a hydrogen atom, a methyl group or an ethyl group, at least one of R3 is a methyl group or an ethyl group; $R^4$ is a methyl group or an ethyl group; m is a number in which the sulfo group (—$SO_3^-$) is bonded to the phenyl group at the 5-position of the tetrazole skeleton, and is 1 or 2; n is a number in which $R^2$ is bonded to the phenyl group at the 3-position of the tetrazole skeleton, and is an integer of 0 to 2; p is a number in which the sulfo group (—$SO_3^-$) is bonded to the phenyl group at the 3-position of the tetrazole skeleton, and is 0 or 1; n+p is 1 or more; q is 1 or 2, and when q is 2, each $OR^3$ is arranged adjacent to each other, wherein each OR3 may form a ring with each other; and X represents a hydrogen atom or an alkali metal.

3. The method according to claim 1, wherein, in the step (2), a difference (=$ave_{Tanalyte}$ (%)−$ave_{Tsample}$ (%)) between an average transmittance ($ave_{Tanalyte}$ (%)) of the analysis sample in a wavelength region of 850 to 1000 nm and an average transmittance ($ave_{Tsample}$ (%)) of the specimen in a wavelength region of 850 to 1000 nm is −10% or more and 10% or less.

4. The method according to claim 1, wherein, in the step (2), a total concentration of the transition metal compound and the light-scattering adjustment reagent in an aqueous fraction of the specimen is 750 mmol/L or less.

5. The method according to claim 1, wherein, in the step (2), the transition metal compound is mixed at a ratio of 4.0 mol or more with respect to 1 mol of the coloring reagent.

6. An analyte concentration measuring reagent comprising:
    a coloring reagent;
    an oxidoreductase;
    a light-scattering adjustment reagent; and
    a transition metal compound at a ratio of 4.0 mol or more with respect to 1 mol of the coloring reagent.

7. The analyte concentration measuring reagent according to claim 6, wherein the coloring reagent is 2-substituted benzothiazolyl-3-substituted phenyl-5-substituted sulfonated phenyl-2H-tetrazolium salt represented by the following formula (2):

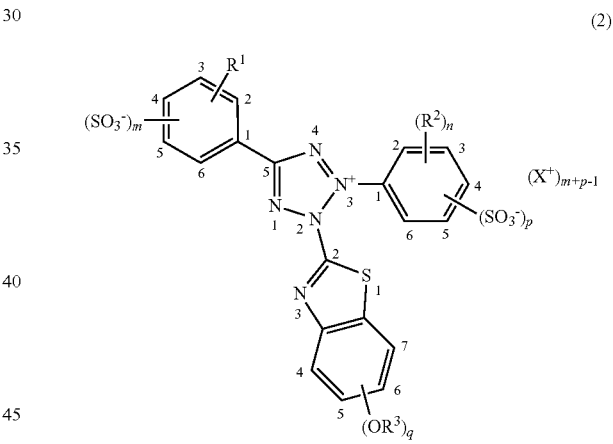

(2)

wherein $R^1$ is any one selected from the group consisting of a hydrogen atom, a hydroxy group, a methoxy group, and an ethoxy group; $R^2$ is any one selected from the group consisting of a nitro group, —$OR^4$, and a carboxyl group; $R^3$ is a hydrogen atom, a methyl group or an ethyl group, at least one of $R^3$ is a methyl group or an ethyl group; $R^4$ is a methyl group or an ethyl group; m is a number in which the sulfo group (—$SO_3^-$) is bonded to the phenyl group at the 5-position of the tetrazole skeleton, and is 1 or 2; n is a number in which $R^2$ is bonded to the phenyl group at the 3-position of the tetrazole skeleton, and is an integer of 0 to 2; p is a number in which the sulfo group (—$SO_3^-$) is bonded to the phenyl group at the 3-position of the tetrazole skeleton, and is 0 or 1; n+p is 1 or more; q is 1 or 2, and when q is 2, each $OR^3$ is arranged adjacent to each other, wherein each OR3 may form a ring with each other; and X represents a hydrogen atom or an alkali metal.

8. A chip for measuring an analyte concentration in a specimen, the chip comprising a reaction unit, wherein the reaction unit comprises the analyte concentration measuring reagent according to claim 6.

9. The chip according to claim 8, wherein the coloring reagent is 2-substituted benzothiazolyl-3-substituted phenyl-5-substituted sulfonated phenyl-2H-tetrazolium salt represented by the following formula (2):

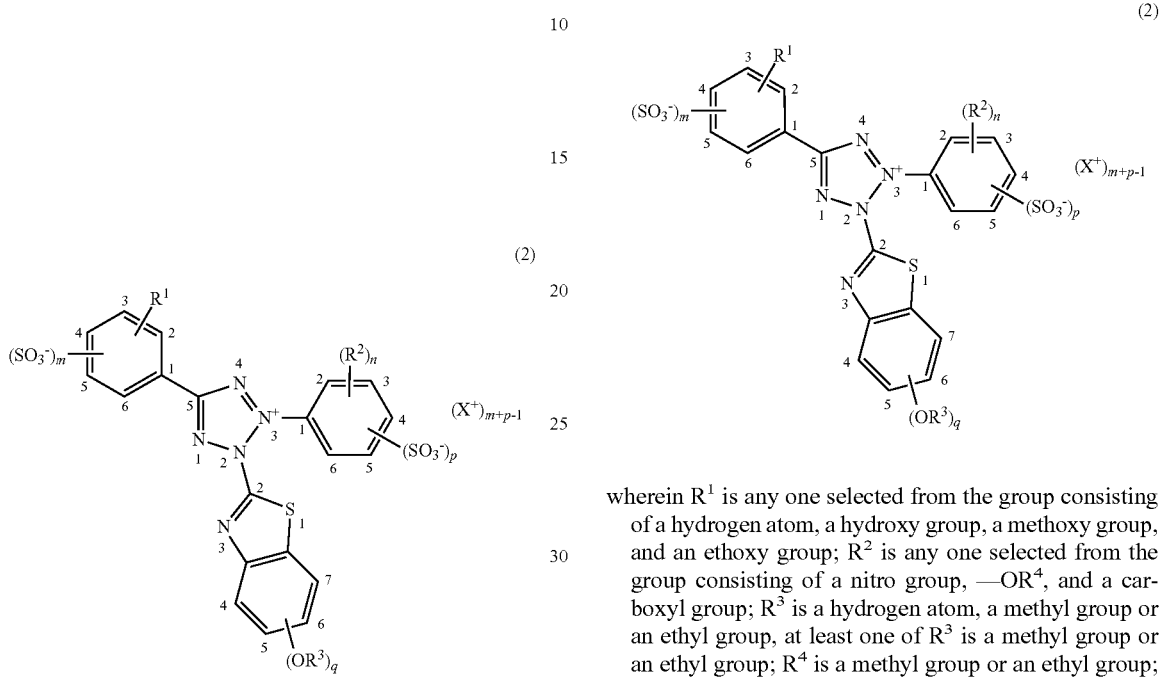

(2)

wherein R¹ is any one selected from the group consisting of a hydrogen atom, a hydroxy group, a methoxy group, and an ethoxy group; R² is any one selected from the group consisting of a nitro group, —OR⁴, and a carboxyl group; R³ is a hydrogen atom, a methyl group or an ethyl group, at least one of R³ is a methyl group or an ethyl group; R⁴ is a methyl group or an ethyl group; m is a number in which the sulfo group (—SO₃⁻) is bonded to the phenyl group at the 5-position of the tetrazole skeleton, and is 1 or 2; n is a number in which R² is bonded to the phenyl group at the 3-position of the tetrazole skeleton, and is an integer of 0 to 2; p is a number in which the sulfo group (—SO₃⁻) is bonded to the phenyl group at the 3-position of the tetrazole skeleton, and is 0 or 1; n+p is 1 or more; q is 1 or 2, and when q is 2, each OR³ is arranged adjacent to each other, wherein each OR³ may form a ring with each other; and X represents a hydrogen atom or an alkali metal.

10. The chip according to claim 9, wherein the reaction unit further comprises a transition metal compound at a ratio of 4.0 mol or more with respect to 1 mol of the coloring reagent.

11. An analyte concentration measuring reagent, comprising:

a coloring reagent comprising 2-substituted benzothiazolyl-3-substituted phenyl-5-substituted sulfonated phenyl-2H-tetrazolium salt represented by the following formula (2):

wherein R¹ is any one selected from the group consisting of a hydrogen atom, a hydroxy group, a methoxy group, and an ethoxy group; R² is any one selected from the group consisting of a nitro group, —OR⁴, and a carboxyl group; R³ is a hydrogen atom, a methyl group or an ethyl group, at least one of R³ is a methyl group or an ethyl group; R⁴ is a methyl group or an ethyl group; m is a number in which the sulfo group (—SO₃⁻) is bonded to the phenyl group at the 5-position of the tetrazole skeleton, and is 1 or 2; n is a number in which R² is bonded to the phenyl group at the 3-position of the tetrazole skeleton, and is an integer of 0 to 2; p is a number in which the sulfo group (—SO₃⁻) is bonded to the phenyl group at the 3-position of the tetrazole skeleton, and is 0 or 1; n+p is 1 or more; q is 1 or 2, and when q is 2, each OR³ is arranged adjacent to each other, wherein each OR³ may form a ring with each other; and X represents a hydrogen atom or an alkali metal;

an oxidoreductase;

a light-scattering adjustment reagent comprising an aromatic hydrocarbon having at least one sulfonic acid group or a salt thereof; and a transition metal compound at a ratio of 4.0 mol or more with respect to 1 mol of the coloring reagent.

12. A chip for measuring an analyte concentration in a specimen, the chip comprising a reaction unit, wherein the reaction unit comprises the analyte concentration measuring reagent according to claim 11.

13. The chip according to claim 12, wherein the reaction unit further comprises a transition metal compound at a ratio of 4.0 mol or more with respect to 1 mol of the coloring reagent.

14. The analyte concentration measuring reagent according to claim 6, wherein the light-scattering adjustment reagent comprises an aromatic hydrocarbon having at least one sulfonic acid group or a salt thereof.

15. The analyte concentration measuring reagent according to claim 7, wherein the light-scattering adjustment reagent comprises an aromatic hydrocarbon having at least one sulfonic acid group or a salt thereof.

* * * * *